(12) United States Patent
Suda et al.

(10) Patent No.: US 7,320,867 B2
(45) Date of Patent: *Jan. 22, 2008

(54) LINKER COMPOUND, LIGAND, AND PRODUCING METHOD THEREOF

(75) Inventors: Yasuo Suda, Kagoshima (JP); Akio Arano, Nagoya (JP); Shoichi Kusumoto, Minoo (JP); Michael Sobel, Seattle, WA (US)

(73) Assignees: Japan Science and Technology Agency, Saitama (JP); National University Corporation Kagoshima University, Kagoshima (JP)

( * ) Notice: Subject to any disclaimer, the term of this patent is extended or adjusted under 35 U.S.C. 154(b) by 139 days.

This patent is subject to a terminal disclaimer.

(21) Appl. No.: 10/526,775

(22) PCT Filed: Sep. 8, 2003

(86) PCT No.: PCT/JP03/11417

§ 371 (c)(1),
(2), (4) Date: Mar. 8, 2005

(87) PCT Pub. No.: WO2004/022583

PCT Pub. Date: Mar. 18, 2004

(65) Prior Publication Data

US 2006/0030699 A1    Feb. 9, 2006

(30) Foreign Application Priority Data

Sep. 9, 2000   (JP) ............................. 2002-263412
Jul. 2, 2003   (JP) ............................. 2003-190568

(51) Int. Cl.
G01N 33/53   (2006.01)
G01N 33/532  (2006.01)
C12P 7/58    (2006.01)
C07K 1/13    (2006.01)

(52) U.S. Cl. ................. 435/7.1; 435/7.92; 435/137; 435/961; 435/287.2; 435/970; 530/402; 530/404; 530/411; 436/544

(58) Field of Classification Search ............ 435/7.1, 435/7.92, 137, 961, 287.2, 970; 530/402, 530/404, 411; 436/544

See application file for complete search history.

(56) References Cited

U.S. PATENT DOCUMENTS 5,714,166 A * 2/1998 Tomalia et al. ............ 424/486
6,756,354 B2 * 6/2004 Nelson ...................... 514/2

FOREIGN PATENT DOCUMENTS

| EP | 0869126 B1 | 4/1998 |
|---|---|---|
| JP | 2002-080488 A | 3/2002 |
| JP | 2002080488 | * 3/2002 |
| JP | 2003-83969 A | 3/2003 |
| WO | WO 01/86301 A1 | 11/2001 |

OTHER PUBLICATIONS

"Synthesis of a conjugate having heparin partial structure and a distal disulfide group and its application to chip technology", A. Arano et al., Tentative Lecture Proceedings II in the 79th Spring Meeting, Chemical Society of Japan, Mar. 15, 2001, p. 1042 (4 G3 05).
"Preparation of a novel clustered oligosaccharide-ligand containing multi-units of heparin partial structure and its application for chip technology", A. Arano et al., Chemical Society of Japan, the 82nd Fall Meeting, Sep. 10, 2002, p. 137 (1C1-11).
"Synthesis of Sugar Arrays in Microtiter Plate", F. Fazio et al., J. Am. Chem. Soc. 2002, 124, pp. 14397-14402.
"Carbohydrate Chips for Studying High-Throughput Carbohydrate Protein Interactions", S. Park et al., J. Am. Chem. Soc. 2004, 126, pp. 4812-4819.
"Nonstatistical binding of a protein to clustered carbohydrates", N. Horan et al., PNAS, Oct. 12, 1999, vol. 96, No. 21, pp. 11782-11786.
"Carbohydrate Arrays for the Evaluation of Protein Binding and Enzymatic Modification", B. T. Houseman et al., Chemistry & Biology, vol. 9, pp. 443-454, Apr. 2002.
"Using Model Substrates To Study the Dependence of Focal Adhesion Formation on the Affinity of Integrin-Ligand Complexes", M. Kato et al., Biochemistry 2004, 43, pp. 2699-2707.
"Probing Protein-Carbohydrate Interactions with Microarrays of Synthetic Oligosaccharides", D. M. Ratner et al., ChemBioChem, 2004, 5, pp. 379-382.
"Oligosaccharide microarrays to decipher the glyco code", T. Feizi et al., Nature Reviews, Jul. 2004, vol. 5, pp. 582-588.
Akio Arano et al., "Heparin Bubun Kozo o Yusuru Cluster-ka Oligo-torui Ligand no gosei to chip Technology eno Oyo", CSJ: The chemical Society of Japan Dai 82 Shuki Nenkai (2002) Kagaku Kankeigaku Kyogikai Kenkyu Happyokai Rengo Toronkai Godo Taikai, Sep. 10, 2002, p. 137 (1C1-11).
Yasuo Sumida, "Ryusanka Tennen Tato no Kino Domain Kozo no Saikochiku to Sensor Chip eno Oyo", CSJ: The Chemical Society of Japan Dai 81 Shunki Nenkai 2002 Nen Koen Yokoshu II, Mar. 2002, p. 949 (1F6-33).

(Continued)

Primary Examiner—Long V. Le
Assistant Examiner—Shafiqul Haq
(74) Attorney, Agent, or Firm—Harness, Dickey & Pierce, P.L.C.

(57) ABSTRACT

A linker compound has a structure represented by general formula (1) below, where n is an integer of 1 to 6, and X has a structure serving as a multi-branched structure moiety including three or four hydrocarbon derivative chains each having an aromatic amino group at an end and a carbon-nitrogen bond in a backbone. A ligand includes the linker compound and a sugar introduced into the linker compound (1)

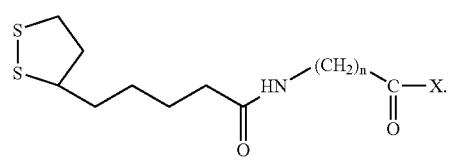

25 Claims, 2 Drawing Sheets

OTHER PUBLICATIONS

Hideki Hayashi et al., "Ryusanka Oligo-to no Shugoka, Biotin-ka oyobi Sono Hyomen Plasmon Kyomei eno Oyo", CSJ: The Chemical Society of Japan Dai 79 Shunki Nenkai (2001) Koen Yokoshu II, Mar. 2001, p. 1042 (4G304).

Akio Arano et al., "Disulfide Ketsugo O Yusuru Linker O Ketsugo saseta Heparin Bubun Kozo no Gosei to Chip Technology eno Oyo", CSJ: The Chemical Society of Japan Dai 79 Shunki Nenkai (2001) Koen Yokoshu II, Mar. 2001, p. 1042 (4G305).

Koshida S et al., An efficient method for the assembly of sulfated oligosaccharides using reductive amination., Tetrahedron Lett., 2001, vol. 42, pp. 1293 to 1296.

Koshida S et al., Synthesis of oligomeric assemblies of a platelet-binding key disaccharide in heparin and their biological activities., Tetrahedron Lett. 2001, vol. 42, pp. 1289 to 1292.

Yasuo Sumida et al., Ryusanka Oligo-to o Koteika shita Chip no Kaihatsu to Hyomen Plasmon Kyomeiho eno Oyo, Seikagaku, Aug. 25, 2002, vol. 74, No. 8, p. 849 (3P-047).

Hideki Hayashi et al., "Ryusanka Oligo-to no Shugoka, Biotin-ka to Sono Sensor Chip eno Oyo", Dai 23 Kai The Japanese Society of Carbohydrate Research Nenkai Yoshishu, Jul. 2002, p. 75 (PI-05).

Korean Office Action dated May 29, 2006 with English translation.

* cited by examiner

US 7,320,867 B2

LINKER COMPOUND, LIGAND, AND PRODUCING METHOD THEREOF

RELATED APPLICATIONS

This is a US national phase filing under 35 U.S.C. § 371 of PCT/JP/03/11417 filed Sep. 8, 2003 and claims priority from JP 2002-263412 filed Sep. 9, 2002 and JP 2003-190568 filed Jul. 2, 2003.

TECHNICAL FIELD

The present invention relates to a linker compound which can immobilize a sugar such as an oligosaccharide onto a protein-analyzing supporter such as a sensor chip or the like used for surface plasmon resonance. The invention also relates to a ligand which includes the linker compound and a sugar introduced thereinto, a ligand carrier, and producing methods of such linker compounds, ligands, and ligand carriers.

BACKGROUND ART

Various intravital saccharides play an important role in a mechanism for sustaining activities and lives of living organisms. In order to precisely reveal such functions of saccharides, the functions of saccharides need to be analyzed based on complex structures of the saccharides. The functions of saccharides are analyzed through a method in which an oligosaccharide whose structure has been revealed is used to reproduce a structure of the saccharide part by part so as to clarify a relationship between the structure and function of the entire saccharide.

The surface plasmon resonance (SPR) method is for example known as a method for analyzing functions of saccharides. That is, a ligand including an oligosaccharide which imitates a moiety of a saccharide is introduced onto a surface of a sensor chip. The sensor chip including the ligand introduced thereon is used to identify a substance such as a protein which specifically interacts with the oligosaccharide. This makes it possible to accurately evaluate a biological activity based on a structure of the oligosaccharide.

However, since a single molecule of oligosaccharide is not as active, oligosaccharides need to be collected on a sensor chip in case of evaluating a biological activity of the oligosaccharides. That is, collected oligosaccharides are used to analyze their interaction with a substance such as a protein, thereby making it possible to accurately evaluate a biological activity of the oligosaccharides.

Accordingly, as disclosed in Japanese Laid-Open Publication No. 836969/2003 (Tokukai 2003-836969; published on Mar. 19, 2003) (Document 1) and "Tentative Lecture Proceedings II in the 79th Spring Meeting, Chemical Society of Japan, Mar. 15, 2001, p. 1042" (Document 2), the inventors have so far obtained a linker compound whose molecule has a moiety immobilizable onto a sensor chip and a moiety capable of taking in an oligosaccharide. The inventors have also obtained a ligand which includes the linker compound and one unit (molecule) or two units of oligosaccharides introduced into the linker compound. Thus, the inventors have found that the ligand can collect oligosaccharides on a sensor chip and thereby introduce the oligosaccharides onto the sensor chip.

However, although the conventional ligand can arrange the sugar chain of the oligosaccharides two-dimensionally on a surface of the sensor chip, there is still a technical problem in that it is difficult to obtain the arrangement with high reproducibility.

That is, in case of collecting plural molecules of oligosaccharide on a surface of the sensor chip so as to analyze a biological activity of the oligosaccharides, the sugar chain of the oligosaccharides needs to be uniformly collected so as to observe with high reproducibility an interaction between the oligosaccharides and a protein. Particularly, in order to observe biological activities of the oligosaccharides, three to four units of oligosaccharides need to be collected on a surface of the sensor chip, and arranged two-dimensionally on the sensor chip with high reproducibility. This arrangement makes it possible to evaluate a biological activity of the oligosaccharides with high reproducibility.

However, the conventional ligand includes one or two units of oligosaccharides per one unit (molecule). In other words, in the conventional ligand, one linker compound binds to one or two oligosaccharides. Therefore, in order to observe a biological activity of the oligosaccharides, three or more units of oligosaccharides need to be collected on a surface of the sensor chip by collecting and arranging the ligands thereon in such a manner as to increase the ligand concentration.

In case of collecting oligosaccharides according to such a method, it is difficult to control the interval of the sugar chains of the oligosaccharides at a predetermined interval so as to obtain an oligosaccharide arrangement with high reproducibility. Therefore, with the conventional ligand, it is not possible to observe a biological activity of oligosaccharides with high reproducibility. This may cause a difficulty in revealing structures of saccharides, or evaluating biological activities of oligosaccharides.

The present invention was made to solve the above problems. It is an object of the present invention to provide a novel linker compound with which saccharides can be arranged two-dimensionally on a protein-analyzing supporter or the like with high reproducibility, a novel ligand which includes the linker compound and sugar molecules introduced thereinto, a ligand carrier, and a producing method thereof.

DISCLOSURE OF INVENTION

The inventors diligently studied to solve the above problems. As a result, the inventors found that three or four units of sugar molecules can be arranged two-dimensionally on a protein-analyzing supporter with high reproducibility by using a novel linker compound which includes a moiety capable of taking in three or four units of sugar molecules and a moiety capable of binding to the supporter used to detect and separate a protein which specifically interacts with the sugar molecule, thereby completing the present invention.

That is, in order to solve the above problems, a linker compound has a structure represented by following general formula (1), where n is an integer of 1 to 6, and X has a structure serving as a multi-branched structure moiety including three or four hydrocarbon derivative chains, wherein the hydrocarbon derivative chains each include an aromatic amino group at an end, and may or may not include a carbon-nitrogen bond in a backbone.

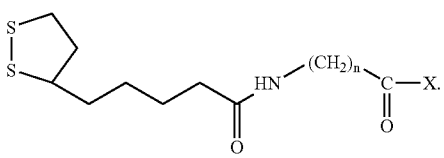

(1)

As used herein, the "hydrocarbon derivative chain" refers to a hydrocarbon chain of carbon and hydrogen, in which part of the carbon atoms and hydrogen atoms may be replaced with other atoms or substitutients. That is, the hydrocarbon derivative chain includes an aromatic amino group at an end, and part of the carbon-carbon bonds (C—C bonds) constituting the backbone structure of the hydrocarbon chain may be replaced with a carbon-nitrogen bond (C—N bond), a carbon-oxygen bond (C—O bond), or an amide bond (CO—NH bond).

According to the above arrangement, the linker compound has an aromatic amino group serving as a moiety capable of easily taking in a sugar. molecule. Since the aromatic amino group is included in each hydrocarbon derivative chain, three or four units of sugar molecules can be introduced into the linker compound. In addition, the linker compound has an S—S bond serving as a moiety immobilizable onto a protein-analyzing supporter.

Therefore, with the linker compound, three or four units of sugar molecules can be collected on the supporter and introduced into the linker compound. In addition, since three or four units of sugar molecules are introduced into one linker compound, three or four units of sugar molecules can be arranged with high reproducibility on a surface of the supporter. This makes it possible to observe an interaction between the sugar molecules and a protein on the surface of the supporter. Further, biological activities of sugar molecules can be evaluated with high reproducibility.

In a linker compound having a structure represented by the general formula (1), it is preferable that X have a structure represented by following formula (2), where $m^1$, $m^2$, and $m^3$ are independently an integer of 1 to 6.

Since X in the linker compound has three hydrocarbon derivative chains, the linker compound enables three units of sugar molecules to be introduced onto the supporter. This makes it possible to control an interval among the three units of sugar molecules on a surface of the supporter so as to arrange the sugar molecules with high reproducibility, thereby evaluating biological activities of the sugar molecules with high reproducibility.

In addition, in a linker compound having a structure represented by the general formula (1), it is preferable that X have a structure represented by following formula (3), where $m^4$, $m^5$, $m^6$, $m^7$, $p^1$, and $p^2$ are independently an integer of 1 to 6.

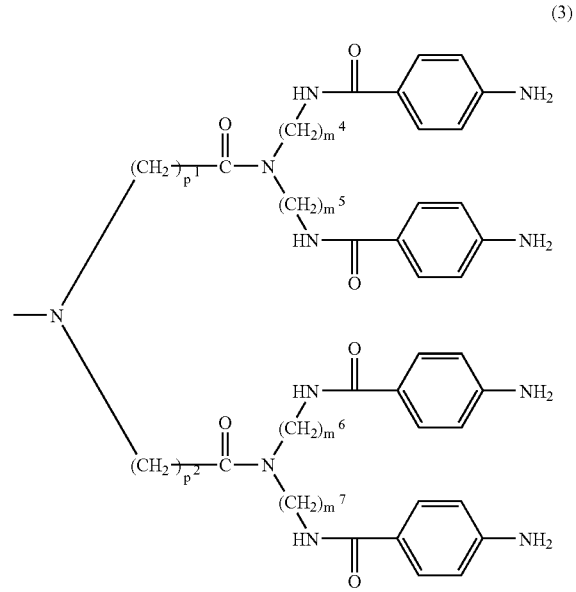

(3)

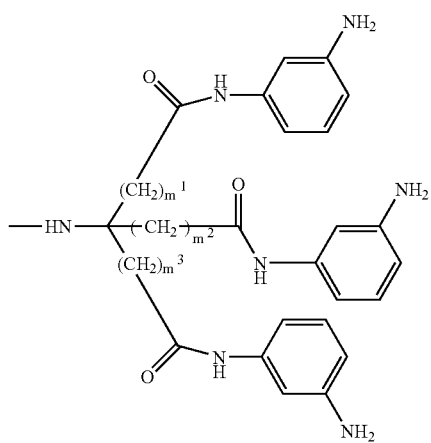

(2)

Since X in the linker compound has four hydrocarbon derivative chains, the linker compound enables four units of sugar molecules to be introduced onto the supporter. This makes it possible to control an interval among the four units of sugar molecules on a surface of the supporter so as to arrange the sugar molecules with high reproducibility, thereby evaluating biological activities of the sugar molecules with high reproducibility.

In addition, in order to solve the above problems, a ligand of the present invention includes the aromatic amino group of the linker compound and a sugar molecule introduced into any of the aromatic amino groups of the linker compound.

It is preferable, specifically, that a ligand have a structure represented by following general formula (4), wherein $m^1$, $m^2$, $m^3$, and n are independently an integer of 1 to 6.

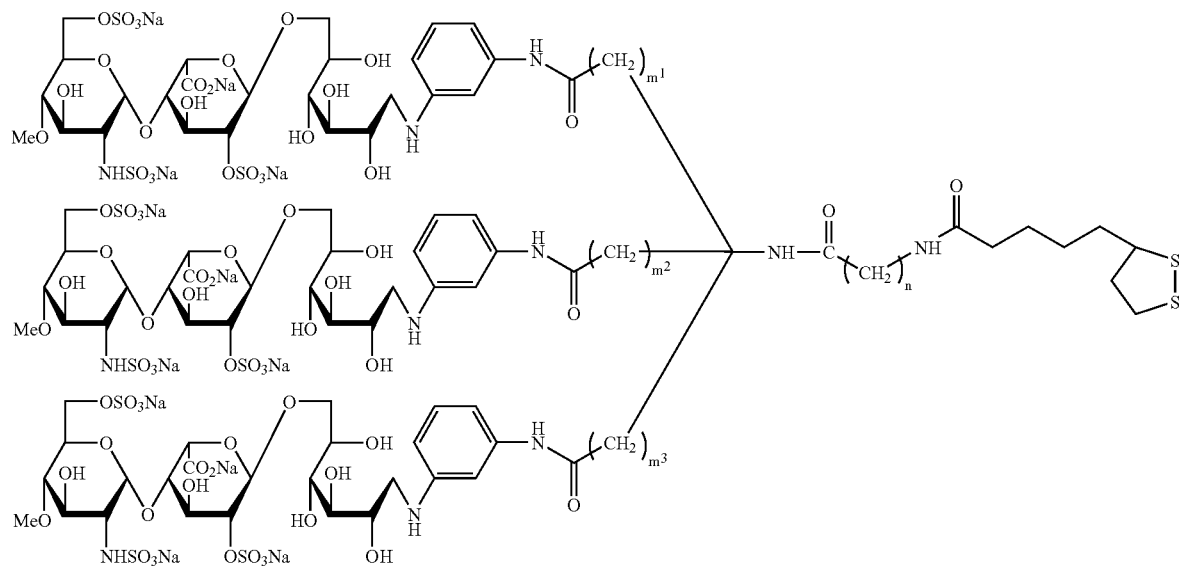
(4)
Otherwise, it is preferable that a ligand have a structure represented by following formula (5), wherein $m^4$, $m^5$, $m^6$, $m^7$, n, $p^1$, and $p^2$ are independently an integer of 1 to 6.
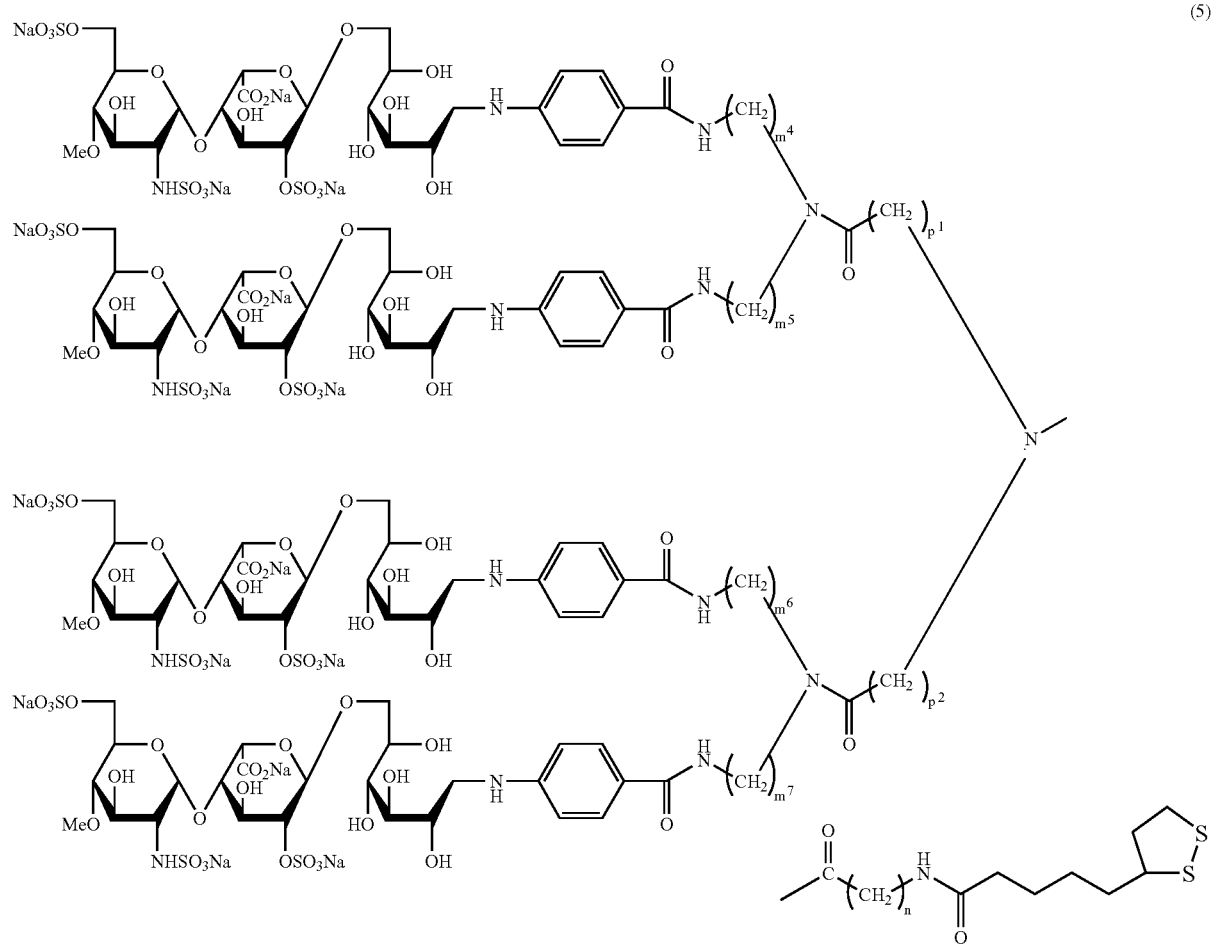
(5)

With any of these ligands, three units of sugar molecules (in the case of a ligand having a structure represented by general formula (4)) or four units of sugar molecules (in the case of a ligand having a structure represented by general formula (5)) can be collected and immobilized on a surface of the protein-analyzing supporter. In this manner, since one ligand has three or four sugar molecules, use of a single ligand enables three or four units of sugar molecules to be collected without collecting a plurality of ligands on the surface of the supporter. This enables biological activities of the sugar molecules to be measured with high reproducibility. Further, a plurality of sugar molecules can be arranged two-dimensionally on the surface of the supporter with high reproducibility. Therefore, with a protein-analyzing supporter on which a ligand of the present invention is immobilized, biological activities of sugar molecules can be evaluated with high reproducibility.

In addition, in order to solve the above problems, a producing method of a linker compound of the present invention includes the steps of: carrying out a condensation reaction between thioctic acid and an amine compound including three or four branched chains each having an aromatic amino group end protected by a protecting group; and deprotecting the protecting group at the aromatic amino group end.

With the above method, a linker compound of the present invention can be obtained which has an S—S bond serving as a moiety immobilizable onto the protein-analyzing supporter, and an aromatic amino group serving as a moiety capable of easily taking in a sugar molecule.

In addition, in order to solve the above problems, a producing method of a ligand of the present invention includes the step of carrying out a reductive amination reaction using the linker compound and a sugar molecule.

With the above method, a ligand of the present invention can be obtained by a reductive amination reaction by which a sugar molecule is easily introduced into a linker compound.

In addition, in order to solve the above problems, a sugar molecule introducing method of the present invention includes the step of causing a solution containing the ligand to come into contact with a supporter whose surface has a metal.

With the above method, an S—S bond of the ligand (linker compound included in the ligand) can be converted to a bond with the metal coating the surface of the supporter, so as to immobilize the ligand onto the surface of the supporter. Therefore, the sugar molecules binding to the linker compound can be arranged on the surface of the supporter by a simple method in which a solution including the ligand is brought into contact with a supporter.

In addition, in order to solve the above problems, a ligand carrier of the present invention includes the ligand immobilized on a supporter whose surface has a metal.

According to the arrangement, the ligand can be firmly immobilized on a surface of the supporter through a sulfur-metal bond, thereby providing a ligand carrier including a plurality of sugar molecules arranged on the surface of the supporter with high reproducibility. Therefore, with the ligand carrier, an interaction between the sugar molecules included in the ligand and a substance such as a protein which interacts with sugar molecules can be observed with high reproducibility, thereby making it possible to quantitatively evaluate biological activities of sugar molecules.

For a fuller understanding of the nature and advantages of the invention, reference should be made to the ensuing detailed description taken in conjunction with the accompanying drawings.

BEST MODE FOR CARRYING OUT THE INVENTION

Figure 1:
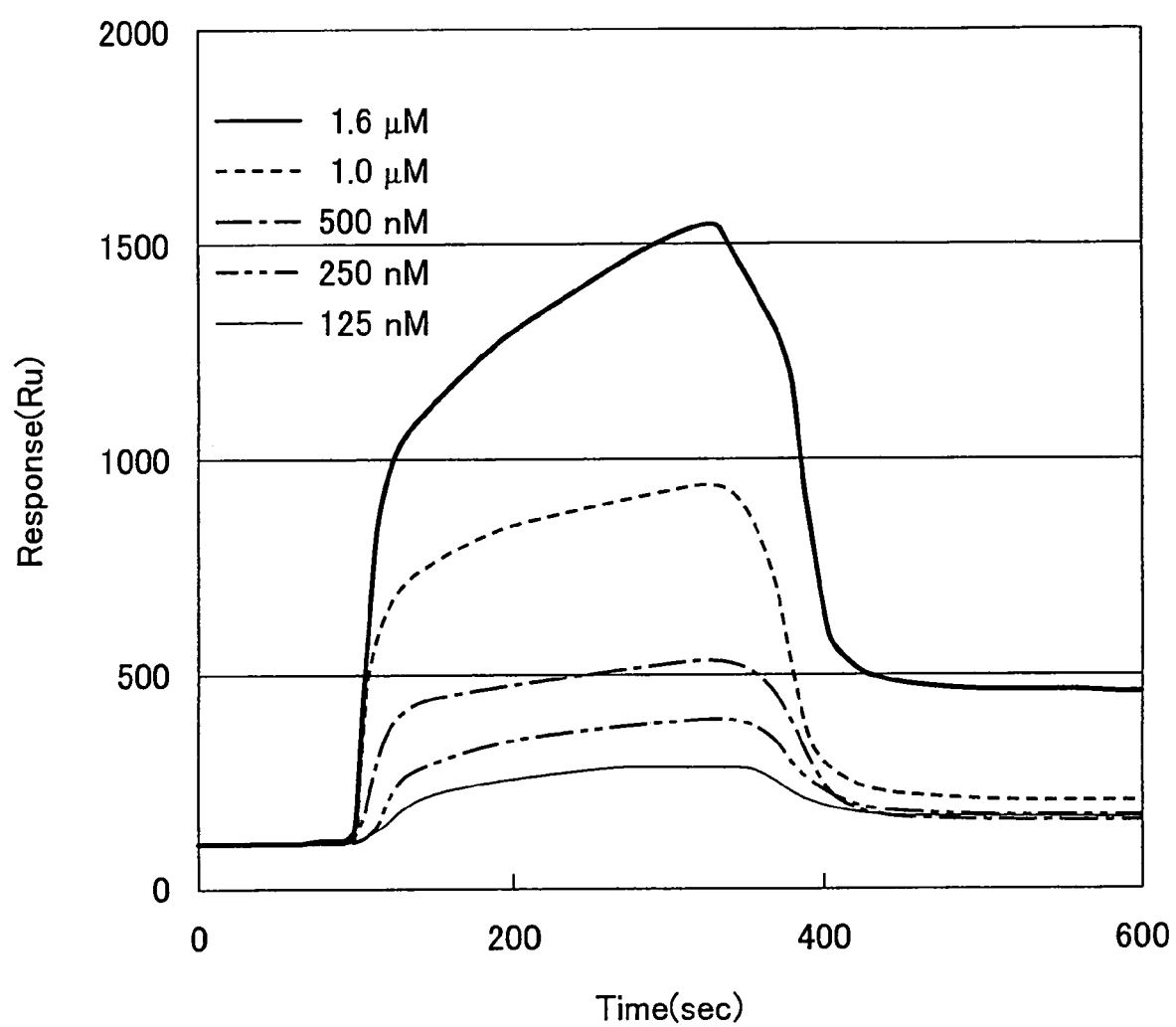
FIG. 1 is a graph showing a result of an SPR measurement measuring the bonding between a ligand-introduced chip, on which a ligand of the present example is immobilized, and rvWF.

In the following, the present invention will be described in detail. However, the present invention is not to be limited by the following description.

A linker compound of the present invention, lying between a protein-analyzing supporter (e.g., an SPR sensor chip or an affinity chromatographic carrier) and a saccharide (hereinafter referred to as a sugar molecule; e.g., an oligosaccharide), is used to immobilize the sugar molecule onto a surface of the supporter. Therefore, the linker compound needs to include, within a molecule, a moiety immobilizable onto the supporter and a moiety capable of easily taking in the sugar molecule.

In addition, an object of the SPR and the affinity chromatography is to identify and separate a substance, such as a protein, which specifically interacts with a sugar molecule. Therefore, the linker compound must not provide a nonspecific interaction with a substance such as a protein.

Accordingly, as shown in general formula (1), the linker compound of the present invention has a disulfide bond (S—S bond) serving as a moiety immobilizable onto the supporter. The sulfur (S) of the disulfide bond for example forms a sulfur-gold bond (S—Au bond) with gold coating the surface of the protein-analyzing supporter, thereby firmly bonding with the supporter.

In addition, the linker compound has a multi-branched moiety including a plurality of amino groups. The multi-branched moiety serves as a moiety which can easily take in a sugar molecule, so that a plurality of sugar molecules can be two-dimensionally arranged on the surface of the protein-analyzing supporter, and that an interval between sugar chains of individual sugar molecules can be controlled. That is, the multi-branched moiety of the linker compound of the present invention has a structure represented by X of general formula (1), wherein X, as described above, has a structure including three or four hydrocarbon derivative chains which contain an aromatic amino group at an end, and may contain a carbon-nitrogen bond or amide bond in the backbone. It is to be noted, in general formula (1), that n is not limited provided that it is an integer of 1 to 6.

An amino group of the aromatic amino group (—NH$_2$ group) undergoes a reductive amination reaction with a sugar molecule such as an oligosaccharide to provide a substrate for taking in the sugar molecule. That is, the amino group included in the linker compound reacts with an aldehyde group (—CHO group) or a ketone group (—CRO group, where R is a hydrocarbon group) produced by an equilibration within the sugar molecule. By continuously reducing the Schiff base formed by the reaction, the sugar molecule can be easily introduced into the aromatic amino group.

Therefore, with the three or four hydrocarbon derivative chains, X in general formula (1) provides a structure serving as a multi-branched moiety which includes aromatic amino groups capable of taking in the sugar molecule. Since the sugar molecule such as an oligosaccharide is introduced into each aromatic amino group included in the multi-branched moiety, it becomes possible to arrange a plurality of sugar molecules two-dimensionally on the surface of the protein-analyzing supporter with high reproducibility through the linker compound having the structure represented by general formula (1).

Specifically, as shown in general formula (2), X provides a branched structure formed by three hydrocarbon derivative chains binding to a carbon atom (C) at the opposite end of the aromatic amino groups. The —NH— binds to the carbon atom. X has the multi-branched moiety including three hydrocarbon derivative chains due to the binding between the carbon atom and —NH— group. It is to be noted, in general formula (2), that $m^1$, $m^2$, and $m^3$ are not limited provided that they are an integer of 1 to 6. The integers represented by $m^1$, $m^2$, and $m^3$ may be mutually different, or may be the same either partly or completely. Above all, in view of ease of production of the compound having the multi-branched moiety, it is preferable that $m^1$ to $m^3$ be mutually the same integer, 2 in particular.

Alternatively, as shown in general formula (3), X may have a two double-branched structure each formed by two hydrocarbon derivative chains bonding to a nitrogen atom (N) at the opposite end of the aromatic amino groups. In this case, the nitrogen atoms of two double-branched structures bond to a single nitrogen atom through the —CO—CH$_2$— group to form a branched structure. In this case, X provides a structure serving as a multi-branched moiety including four hydrocarbon derivative chains. It is to be noted, in general formula (3), that $m^4$, $m^5$, $m^6$, and $m^7$ are not limited provided that they are an integer of 1 to 6. The integers represented by $m^4$, $m^5$, $m^6$, and $m^7$ may be mutually different, or may be the same either partly or completely. Above all, in view of ease of production of the compound having the multi-branched moiety, it is preferable that $m^4$ to $m^7$ be mutually the same integer, 2 in particular. In addition, $p^1$ and $p^2$ are not limited provided that they are an integer of 1 to 6. The integers represented by $p^1$ and $p^2$ may be mutually different or the same. Above all, in view of ease of production, it is preferable that $p^1$ and $p^2$ be mutually the same integer, 1 in particular.

Thus, X provides a structure serving as a multi-branched moiety having a branched structure formed by bonding a plurality of hydrocarbon derivative chains with an atom such as a carbon atom or nitrogen atom. It is to be noted that although it is preferable that the plurality of hydrocarbon derivative chains included in X all have the same structure, they may have different structures so long as they contain an aromatic amino group at an end.

As described above, the linker compound having the structure represented by general formula (1) has an S—S bond capable of forming a bond with a protein-analyzing supporter, and an amino group capable of forming a bond with a sugar molecule such as an oligosaccharic chain. Therefore, since the linker compound is immobilized on a protein-analyzing supporter for example by an S—Au bond, the linker compound allows the sugar molecule to be firmly and easily bonded with a surface of the supporter.

In addition, since the linker compound has a multi-branched moiety with aromatic amino groups attached to the respective ends of the multi-branched moiety, a ligand (to be mentioned later) obtained by introducing a sugar molecule in the linker compound can be used to effectively collect sugar molecules on the surface of the supporter. In addition, since the ligand including the linker compound has a multi-branched moiety, the ligand including the linker compound, when bonded to a surface of the supporter, allows a plurality of sugar molecules to be two-dimensionally arranged with high reproducibility.

Moreover, with the linker compound, the influence of any non-specific interaction with a protein can be ignored almost completely. Therefore, the use of the linker compound of the present invention allows a biological activity of sugar molecules to be evaluated with high reproducibility.

The linker compound is produced by a producing method described below. That is, the linker compound is prepared by the condensation reaction of thioctic acid with an amine compound including three or four branched chains whose aromatic amino group ends are protected by a protecting group. The reaction deprotects the protecting group at the aromatic amino group ends and yields the linker compound.

The thioctic acid has a structure represented by the following general formula (6).

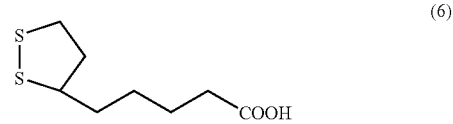

(6)

The amine compound is not particularly limited provided that it includes a branched chain which has an aromatic amino group end protected by a protecting group. The amine compound only needs to have a structure equivalent to the multi-branched moiety of the linker compound.

Therefore, the branched chain only needs to have a structure included in the hydrocarbon derivative chain except that the hydrocarbon derivative chain has the aromatic amino end protected by a protecting group instead of the aromatic amino group. That is, in the branched chain, part of the carbon and hydrogen atoms in the hydrocarbon chain consisting of carbon and nitrogen may be replaced with by other atoms or substituents. More specifically, the branched chain, having an aromatic amino group end protected by a protecting group, may be modified so that part of the carbon-carbon bonds (C—C bonds) in the backbone structure of the hydrocarbon chain are replaced with a carbon-nitrogen bond (C—N bond) or a carbon-oxygen bond (C—O bond).

The protecting group is a substituent which is introduced to prevent an amino group of the aromatic amino group from undergoing the condensation reaction. The protecting group is not specifically limited provided that it is not affected when deprotecting a protecting group for a secondary aromatic amino group. Examples of such protecting groups include a t-butoxycarbonyl group (—COOC (CH$_3$)$_3$ group; referred to as a Boc group), a benzyl group, and an arylcarbamate group (—COOCH$_2$CH═CH$_2$, Alloc group).

Examples of the amine compound are compounds having a structure represented by the following general formulae (7) and (8).

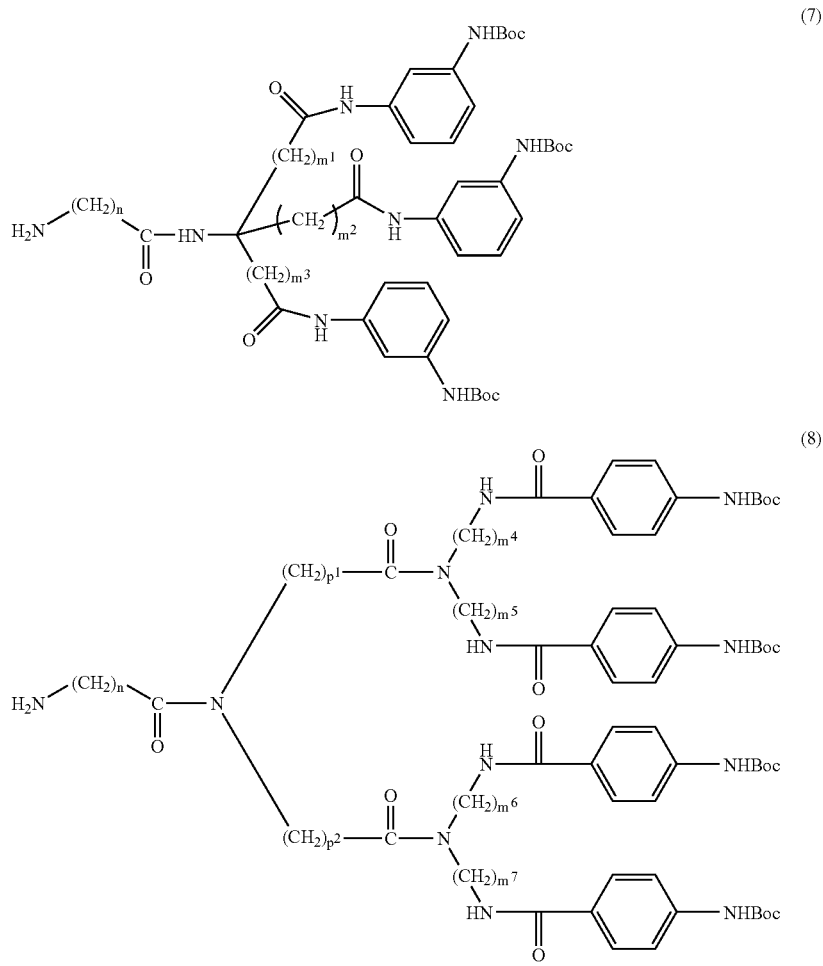

(7)

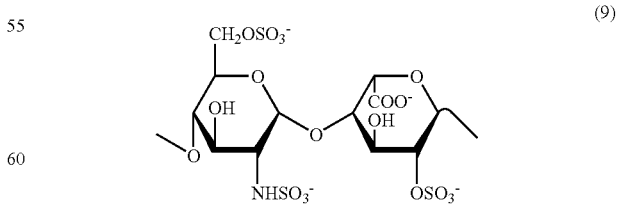

(8)

It is to be noted, in general formulae (7) and (8), that n, $m^1$ to $m^7$, $p^1$ and $p^2$ are independently an integer of 1 to 6. A method for synthesizing the amine compounds will be described in detail in later examples.

In the condensation reaction of the thioctic acid with the amine compound, the carboxyl group of the thioctic acid condenses with the amino group of the amine compound to form an amide bond. Thereafter, the protecting group at the aromatic amino group end is deprotected to free the aromatic amino group and thereby yield the linker compound.

Described in the following is the ligand obtained by introducing a sugar molecule into the aromatic amino group of the linker compound. In the ligand of the present invention, a sugar molecule is introduced into the aromatic amino group. This is due to a continuous reduction of the Schiff base formed by a reaction of the amino group of the linker compound with the aldehyde group or ketone group produced by an equilibration within the sugar molecule. That is, the reductive amination reduction bonds the linker compound with the sugar molecule.

The sugar molecule included in the ligand of the present invention is not specifically limited provided that it is a reducing sugar having a reducing end. Examples of such a sugar molecule include a monosaccharide, an oligosaccharide, and a polysaccharide. The monosaccharide is for example glucose, galactose, and mannose. The oligosaccharide is for example maltose or lactose and a sulfated oligosaccharide, to be mentioned later, having two to ten sugar molecules bonding one another. The polysaccharide is for example heparin, chondroitin sulfate, or heparan sulfate, having 11 or more sugar molecules including monosaccharides and oligosaccharides.

One example of the oligosaccharide is a sulfated oligosaccharide having a specific partial disaccharide structure (GlcNS6S-IdoA2S), represented by following general formula (9), which is contained in sulfated polysaccharic heparin known for having an anticoagulant activity.

(9)

Another example is an oligosaccharide having a structure, represented by following general formula (10), which is the sulfated oligosaccharide having incorporated a glucose at the hydroxyl group serving as a reducing end.

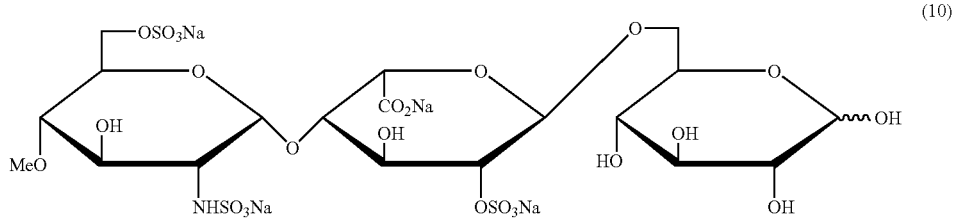

(10)

It is to be noted that the oligosaccharide and polysaccharide may be a homooligosaccharide or homopolysaccharide consisting of a single monosaccharide, or a complex carbohydrate consisting of different monosaccharides or derivatives thereof, or even a complex polysaccharide consisting of different monosaccharides or derivatives thereof, and oligosaccharides. In addition, the sugar molecule may be natural sugar obtained through isolation and purification from nature, or artificially synthetic sugar.

Specifically, the ligand of the present invention has the structure represented by general formula (4). The ligand having the structure represented by general formula (4) is obtained by adding a sugar molecule, represented by general formula (10), to the linker compound represented by general formula (1), where X has a structure represented by general formula (2). Since X represented by general formula (2) has a structure including three hydrocarbon derivative chains, the ligand having the structure represented by general formula (4) includes the linker compound bonded to three units of sugar molecules. It is to be noted, in general formula (4), that, like $m^1$ to $m^3$ in general formula (2), $m^1$ to $m^3$ are not limited provided that they are an integer of 1 to 6. The integers represented by $m^1$ to $m^3$ may be mutually different, or may be the same either partly or completely. Also, n is not specifically limited provided that it is an integer of 1 to 6.

Another ligand of the present invention has a structure represented by general formula (5). The ligand having the structure represented by general formula (5) is obtained by adding a sugar molecule, represented by general formula (10), to the linker compound represented by the general formula (1), where X has the structure represented by general formula (3). Since X represented by general formula (3) has a structure including four hydrocarbon derivative chains, the ligand having the structure represented by general formula (5) includes the linker compound bonded to four units of sugar molecules. It is to be noted, in general formula (5), that, like $m^4$ to $m^7$ in the general formula (3), $m^4$ to $m^7$ are not limited provided that they are an integer of 1 to 6. The integers represented by $m^4$ to $m^7$ may be mutually different, or may be the same either partly or completely. Also, as with $p^1$ and $p^2$ in general formula (3), $p^1$ and $p^2$ are not specifically limited provided that they are an integer of 1 to 6. The intergers represented by $p^1$ and $p^2$ may be mutually different, or may be the same either partly or completely. Also, n is not specifically limited provided that it is an integer of 1 to 6.

Since the ligands include the linker compound and sugar molecule, the ligands can bond to surface metal of a protein-analyzing supporter by forming a sulfur (S)-metal bond, such as a sulfur-gold (S—Au) bond, with the S—S bond contained in the linker compound. This makes it possible to provide a ligand carrier including three or four units of sugar molecules collected and immobilized on the surface of the supporter through the S—Au bond. Therefore, the ligands can be used, for example, to two-dimensionally arrange a plurality of sugar molecules with high reproducibility on the surface of a protein-analyzing supporter and thereby obtain a ligand carrier. The use of the ligand carrier allows a biological activity of the sugar molecules to be evaluated with high reproducibility. It is to be noted that although Cu, Ag, Pt, and the like, as well as Au, can be used for the surface metal of the supporter, Au is particularly preferable.

Thus, the prevent invention also includes a ligand carrier having the ligand of the present invention immobilized on a surface of a supporter through a S-metal bond. The applicable field of the ligand carrier is not limited to the protein analysis. For example, the ligand carrier can be used to analyze substances other than a protein in order to examine an interaction with sugar molecules.

The ligand carrier is formed as the ligand is introduced onto the surface of the supporter. This occurs as each sulfur atom in the S—S bond of the ligand bonds to the surface metal of the supporter by forming a S-metal bond, as a result of a ligand solution including the ligand brought into contact with the supporter with the metal film coating. Specifically, by immersing a protein-analyzing supporter in the ligand solution for a predetermined period of time, or by injecting the ligand solution into the supporter (pouring of the ligand solution onto the surface of the supporter), the S—S bond of the ligand (linker compound included in the ligand) is converted into an S—Au bond with gold or the like coating the surface of the supporter, with the result that the ligand is immobilized on the surface of the supporter.

A solvent usable as a ligand solution is not particularly limited. For example, methanol, water, dimethylacetoamide (DMAc), or a mixture of these solvents may be used. The duration of immersion is about 0.5 to 12 hours, and the amount of injection is about 0.01 to 1 mM.

Thus, since the ligand of the present invention has an S—S bond, it can be easily immobilized on a surface of the protein-analyzing supporter, thus easily introducing a sugar molecule onto the supporter.

It is to be noted, as described above, that the present invention further includes a method for introducing a sugar molecule onto a supporter.

A ligand carrier of the present invention can be used to analyze an interaction between sugar molecules and other substances such as a protein. Specifically, the ligand carrier can be applied to an SPR measurement, affinity chromatography, and the like.

For example, for the purpose of analyzing a protein, an SPR measurement is carried out as follows. That is, using a ligand carrier obtained by immobilizing a ligand of the present invention on a supporter having a metal thin film such as a gold thin film deposited thereon, the ligand carrier is brought into contact with a protein, and a surface plasmon resonance apparatus is used to measure a resonant angle in the usual manner. In this way, the binding behavior of the ligand carrier and the protein can be observed. It is to be noted that glass, plastic, or the like can be used to form the supporter (sensor chip) used for an SPR measurement. Glass is particularly suitable. In addition, the ligand carrier can be brought into contact with the protein by flowing a solution, containing the protein dissolved in a running buffer, onto a surface of the ligand carrier. As the running buffer, a phosphate buffer can be used, for example.

With a ligand carrier of the present invention having the ligand, a plurality of sugar molecules can be two-dimensionally arranged on a surface of the supporter with high reproducibility. Therefore, the ligand carrier makes it possible to observe biological activity of the sugar molecule with high reproducibility, thereby enabling a structure of the sugar molecule to be revealed, and the biological activity of the sugar molecule to be evaluated quantitatively.

In addition, a sensor chip with the ligand, serving as a ligand carrier of the present invention, can be used for an SPR measurement in the manner described below. That is, an interaction of sugar molecules can be observed by detecting a difference between a detection result of an SPR measurement obtained by using a first sensor chip obtained by immobilizing a first sugar molecule on a supporter surface, and a detection result of an SPR measurement obtained by using a second sensor chip obtained by immobilizing a second sugar molecule, having a different end structure from that of the first sugar molecule, on a supporter surface. Between these sensor chips, ligands with different sugar molecules are used for immobilization. Examples of sugar molecules to be compared with each other are lactose and glucose, maltose and glucose, and kojibiose and glucose. Although two sensor chips are used in this example, more than two sensor chips introducing different sugar molecules may be used. It is to be noted that, as used herein, the "end" of a sugar molecule is the side not immobilized on a sensor chip.

The SPR measurement observes resonant angles of the two sensor chips acted on under constant measurement conditions by a protein or other substances which specifically acts on the first sugar molecule. By detecting a difference in resonance angle between the two sensor chips, a specific interaction between the sugar molecule and the protein can be measured.

In addition, a substance used for the observation of an interaction with the sugar molecule is not limited to a protein.

Although two kinds of sensor chips are measured simultaneously according to the above example, it is to be noted that this is not for limitation. More than two kinds of sensor chips may be measured, and the sensor chips do not need to be measured simultaneously. Further, at least one sensor chip may be used without a sugar molecule introduced thereinto. For example, a sensor chip on which only the linker compound is immobilized may be used.

Since the SPR measurement can be made using at least two sensor chips including ligands having the same structure except for the structures of the sugar molecules, a difference in an interaction between at least two sensor chips can be observed as being attributed to the sugar molecules. Therefore, using the described measurement method, a non-specific interaction of a moiety other than the sugar molecule with other substances can be avoided so as to observe a specific interaction between the sugar molecule and other substances.

In the following, the present invention is described in more detail according to Examples and Comparative Example. It is to be noted, however, that the present invention is not limited in any way by the following.

EXAMPLE 1

Synthesis of a Linker Compound

A linker compound of the present invention, having a structure represented by general formula (1), where n is 1 and X is represented by general formula (2), where $m^1$, $m^2$, and $m^3$ are 2, was synthesized according to the following procedure.

As shown in general formula (11) below, three units of t-butylacrylate (Compound 2) was added by Michael addition to nitromethane (Compound 1) in the presence of benzyltrimethylammonium hydroxide in dimethoxyethane at 65° C. to 70° C. As a result, Compound 3 was obtained at the yield of 91%. Subsequently, the nitro group of Compound 3 was reduced using Raney nickel (Raney Ni) under hydrogen atmosphere (6 kg/cm$^2$) in ethanol at 50° C. As a result, Compound 4 was obtained at the yield of 98%.

Thereafter, Compound 4 was condensed with Z-glycine (1.1 equiv.) in the presence of 1-hydroxy-7-azabenzotriazole (HOAt in the formula; 1.1 equiv.) and water-soluble carbodiimide hydrochloride (WSCI.HCl in the formula; 1.1 equiv.) in $CH_2Cl_2$. As a result, a Z-glycine derivative (Compound 5) was obtained at the yield of 85%.

(11)

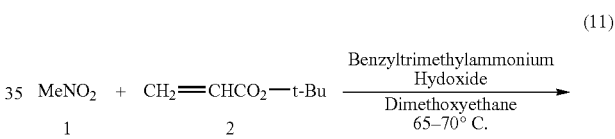

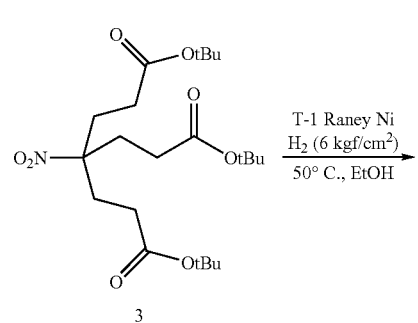

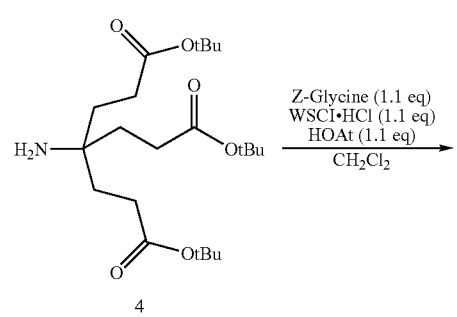

-continued

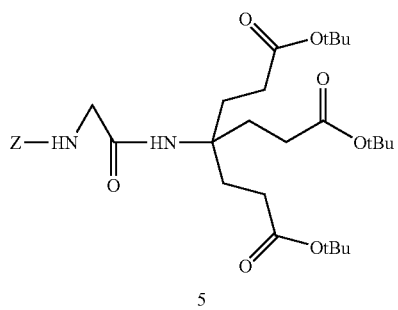

5

More specifically, Compound 4 was obtained according to a method described in G. R. Newkome et al, OPPI BRIEFS, Vol. 28, p. 495, 1996. First, nitromethane (12.2 g, 200 mmol) was dissolved in 50 mL of 1,2-dimethoxyethane. The mixture was heated to 65° C. to 70° C., and 2 mL of 40% benzyltrimethylammonium hydroxide-methanol solution was added thereto to obtain a nitromethane solution. Thereafter, the nitromethane solution was heated to 75° C., and t-butylacrylate (90.8 mL, 620 mmol) was then slowly added dropwise into the nitromethane solution. Then, 1 mL of a 40% benzyltrimethylammonium hydroxide-methanol solution was added four times to the nitromethane solution with the solution temperature kept at 70° C. to 75° C. The resulting solution was stirred for 2.5 hours to obtain a solution of nitromethane and t-butylacrylate as the reaction product. An insoluble matter in the nitromethane/t-butylacrylate reaction solution was then removed by way of decantation to be concentrated. The residue so obtained was dissolved in diethyl ether and then washed twice in each of an ice-cooled 10% aqueous solution of hydrochloric acid, a saturated aqueous solution of sodium hydrogen carbonate, and water to obtain a residue solution. Thereafter, the residue solution was dried using sodium sulfate anhydride as a drying agent. The drying agent was removed by using cerite. The resulting residue solution was concentrated under reduced pressure to obtain a concentrated residue. Thereafter, the concentrated residue was dissolved in ethanol for recrystallization to obtain Compound 3 (81.8 g, 91%) in the form of a white needle crystal.

Then, the crystal of Compound 3 (10 g, 22.4 mmol) and T-1 Raney nickel (6.0 g) were added to anhydrous ethanol (50 mL) and then stirred for 23 hours at 50° C. under hydrogen atmosphere (6 kg/cm²). After that, the T-1 Raney nickel was filter out using cerite to obtain a solution of Compound 3 as the reaction product. The reaction solution of Compound 3 was then concentrated under reduced pressure to obtain a concentrated residue. The concentrated residue so obtained was purified by fractionation silica gel chromatography (solvent: chloroform/methanol=20/1) to obtain Compound 4 (9.2 g, 98% yield) in the form of a white solid.

More specifically, a solution of Compound 4 (2.50 g, 6.02 mmol) dissolved in 2 mL of anhydrous dichloromethane was added at 0° C. to a Z-glycine solution obtained by dissolving Z-glycine (1.26 g, 6.62 mmol), HOAt (0.90 g, 6.62 mmol), and WSCI.HCl (1.27 g, 6.62 mmol) in 28 mL of anhydrous dichloromethane. The resulting solution was stirred for 36 hours at room temperature under argon atmosphere to obtain a reaction solution of Z-glycine and Compound 4. The Z-glycine/Compound 4 reaction solution was mixed with dichloromethane and a 10% aqueous solution of citric acid, and then extracted with dichloromethane. In the extract, the organic layer was washed once in each of water, a saturated aqueous solution of sodium hydrogen carbonate, and water. The organic layer was then dried using sodium sulfate anhydride as a drying agent. The organic layer, from which the drying agent had been filtered out, was concentrated under reduced pressure to obtain a concentrated residue. The concentrated residue so obtained was purified by fractionation silica gel chromatography (solvent: chloroform) to obtain Compound 5 (3.09 g, 85% yield) in the form of a white solid.

An ESI-MS (positive) measurement (time-of-flight mass spetrometer measurement) was conducted on the Compound 5 so obtained. The measurement showed that the m/z (mass/charge ratio) was 629.4 [(M+Na)⁺]. From this, a structure of Compound 5 was confirmed.

Thereafter, as shown in general formula (12) below, the t-butoxycarbonyl groups (—COOC (CH₃)₃ groups; tBu in general formula (12)) of Compound 5 were deprotected using triofluoroacetic acid (hereinafter referred to as TFA) in a mixed solvent of CH₂Cl₂/H₂O=10/1. As a result, Compound 6 was obtained at the yield of 95%.

Thereafter, in the presene of pentafluorophenyldiphenyl phosphate (FDPP in the formula, 4.5 equiv.), diisopropyl ethylamine (DIPEA in the formula, 11 equiv.), and N,N-dimethyl formamide (DMF), the Compound 6 was condensed with an m-phenylenediamine derivative (Compound 7, 10 equiv.) whose amino group is protected by a Boc group. As a result, an N-Boc amine derivative was obtained at the yield of 99%. Thereafter, a catalytic hydrogen reduction was performed in methanol (MeOH in the formula) in the presence of a Pd/C (active-carbon carrier palladium) to deprotect the benzyloxycarbonyl group (Z in the formula) of the Z-glycine which underwent the condensation reaction with the Compound 8. As a result, Compound 9 was obtained at the yield of 79%.

(12)

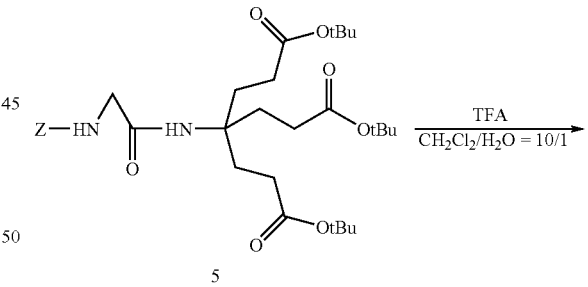

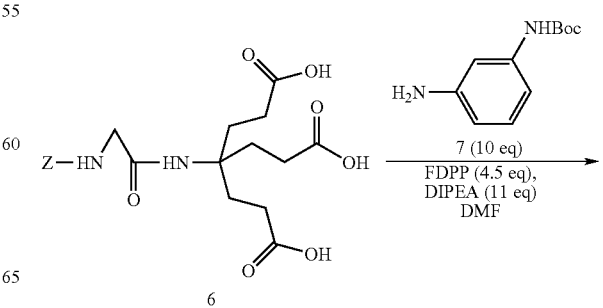

-continued

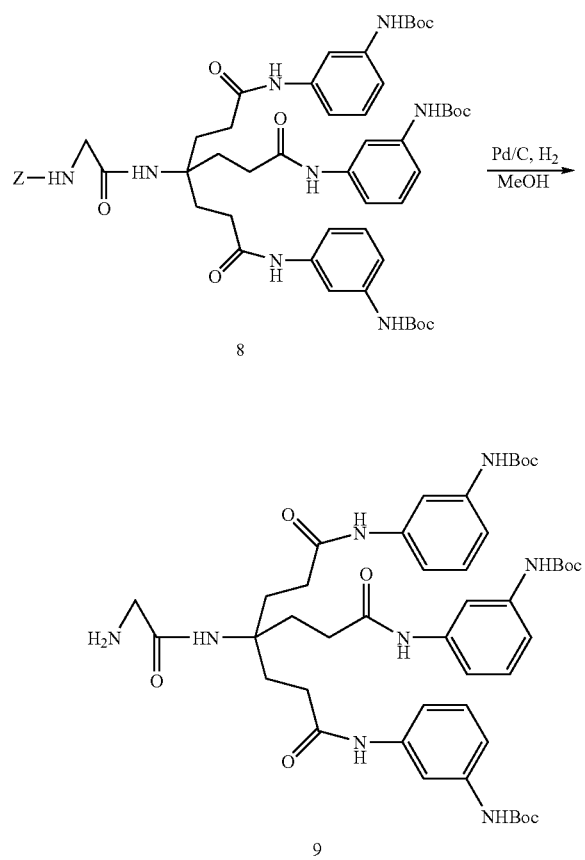

Specifically, Compounds 6 to 9 were obtained by the procedures described below.

Compound 6 was obtained by the following procedure. First, Compound 5 (2.98 g, 4.90 mmol) was dissolved in 15 mL of dichloromethane, and 15 mL of TFA and 1.5 mL of water was added at −10° C. Then, the mixture was stirred for 1.5 hours at room temperature to obtain a solution of Compound 5 as the product of reaction. The reaction solution of Compound 5 was concentrated under reduced pressure to obtain a concentrated residue. After that, a 10% aqueous solution of sodium hydroxide was added to the concentrated residue in an iced bath until pH reached 5, and concentrated hydrochloric acid was added until pH reached 2. As a result, a white solid precipitate was obtained. The white solid so obtained was washed with water to obtain Compound 6 (2.04 g, 95% yield) in the form of a white solid.

An ESI-MS (negative) measurement was conducted on the Compound 6 so obtained. The measurement showed that the m/z was 437.1 [(M−H)$^-$]. Also, a nuclear magnetic resonance ($^1$H-NMR, 400 MHz, d$_6$-DMSO) measurement found that δ=7.34-7.14 (6H, m), 5.00 (1H, s), 3.55 (2h, d, J=5.9 Hz), 3.33 (3H, bs), 2.11 (6H, m), 1.81 (6H, m). From this, a structure of the Compound 6 was confirmed.

Compound 7 was obtained by the following procedure. First, m-phenylenediamine (0.50 g, 4.62 mmol) was dissolved in 35 mL of methanol, and (Boc)2O (1.06 mL, 4.62 mmol) and triethylamine (0.65 mL, 4.65 mmol) were added at 0° C. The mixture was stirred for 24 hours at room temperature, and concentrated under reduced pressure to obtain a concentrated residue. The concentrated residue was purified by fractionation silica gel chromatography (solvent: chloroform/acetone=10/1) to obtain Compound 7 (665 mg, 68% yield) in the form of a white solid.

An ESI-MS (positive) measurement was conducted on the Compound 7 so obtained. The measurement found that the m/z was 231.2 [(M+Na)$^+$]. Also, the result of $^1$H-NMR (400 MHz, CD$_3$Cl) measurement found δ=7.02 (1H, t, J=8.0 Hz), 6.95 (1H, bs), 6.54 (1H, dd, J=2.0 Hz, J=8.0 Hz), 6.41 (1H, bs), 6.35 (1H dd, J=2.2 Hz, J=7.9 Hz), 3.66 (2H, bs), 1.53, 1.50 (9H, s, s). From this, a structure of the Compound 7 was confirmed.

Compound 8 was obtained by the following procedure. First, the Compound 7 (475 mg, 2.28 mmol), FDPP (394 mg, 1.03 mmol), and diisopropyl ethylamine (447 μL, 2.57 mmol) were dissolved in 2 mL of dimethyl formamide anhydride. The mixture was stirred for 29 hours at room temperature under argon atmosphere, mixed with ethyl acetate and water, and extracted with ethyl acetate. The organic layer was washed once in each of 0.5 N hydrochloric acid, water, a saturated aqueous solution of sodium hydrogen carbonate, and saturated salt water. Then, the organic layer was dried using sodium sulfate anhydride as a drying agent. The resulting solution was concentrated under reduced pressure after filtering out the drying agent. The concentrated residue was then purified by fractionation silica gel chromatography (solvent: chloroform/acetone=3/1) to obtain Compound 8 (228 mg, 99% yield) in the form of a white solid.

An ESI-MS (positive) measurement was conducted on the Compound 8. The measurement showed that the m/z was 1009.5 [(M+H)$^+$]. Also, the result of $^1$H-NMR (400 MHz, CD$_3$Cl) measurement found that δ=8.75 (3H, s), 7.67 (3H, s), 7.30-6.95 (18H, m), 6.52 (1H, bs), 5.04 (2H, s), 3.71 (2H, d, J=5.0 Hz), 2.23 (6H, m), 1.97 (6H, m), 1.47 (27H, s). From this, a structure of the Compound 8 was confirmed.

Compound 9 was obtained by the following procedure. First, the Compound 8 (200 mg, 198 μmol) was dissolved in 3 mL of methanol, and 10% Pd/C (62.3 mg) was added. The mixture was stirred for 15 hours at room temperature under hydrogen atmosphere, and concentrated under reduced pressure after filtering out the Pd/C. The resulting concentrated residue was purified by fractionation silica gel chromatography (solvent: chloroform/methanol=8/1) to obtain Compound 9 (136 mg, 78% yield) in the form of a white solid.

An ESI-MS (positive) measurement was conducted on the Compound 9. The measurement showed that the m/z was 875.5 [(M+H)$^+$]. From this, a structure of the Compound 9 was confirmed.

Moreover, as shown in general formula (13), the Compound 9 was condensed with thioctic acid (Compound 10) in the presence of WSCI.HCl (1.0 equiv.) and 1-hydroxybenzotriazole (HOBt in general formula (13); 1.0 equiv.) in CH$_2$Cl$_2$. As a result, a thioctic acid derivative (Compound 11) was obtained at the yield of 75%.

Thereafter, the Boc groups of the Compound 11 were deprotected under acidic condition in the presence of trimethylsilyl chloride (TMSCl in the formula) and phenol (PhOH) in CH$_2$Cl$_2$. As a result, Compound 12 was obtained (32% yield or greater) as a liker compound including three hydrocarbon derivative chains each having an aromatic amino group.

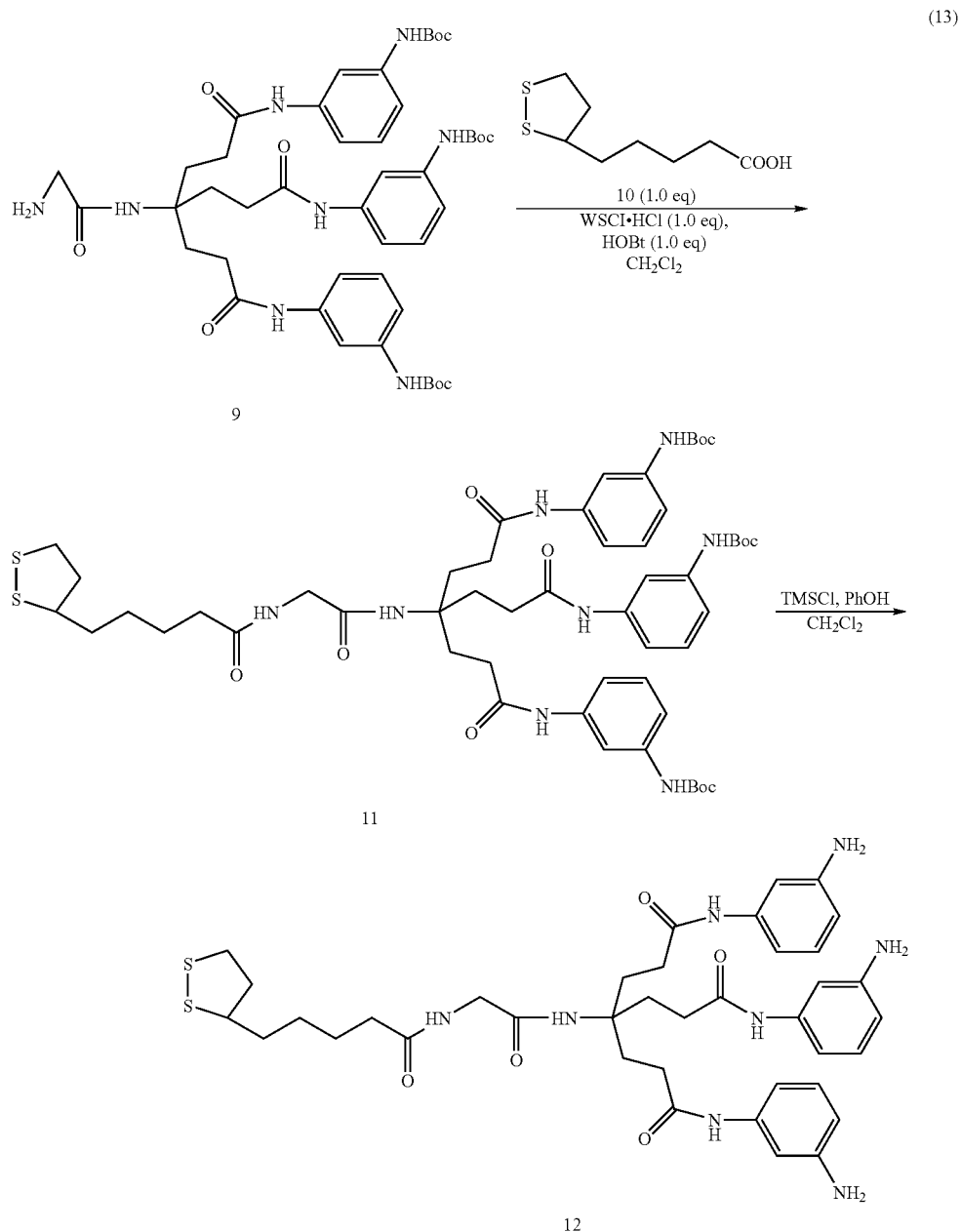

Specifically, Compounds 11 and 12 were obtained by the procedures described below.

Compound 11 was obtained by the following procedure. First, Compound 10 (23.6 mg, 114 mol) and HOBt (15.4 mg, 114 mmol) were dissolved in 2.3 mL of anhydrous dichloromethane, and Compound 9 (2.50 mg, 6.02 mmol) was added at 0° C. The mixture was stirred for 36 hours at room temperature in a shade under argon atmosphere. The resulting solution was mixed with a 10% aqueous solution of citric acid and then extracted with chloroform. The organic layer was washed by a saturated aqueous solution of sodium hydrogen carbonate, and then dried using sodium sulfate anhydride as a drying agent. Thereafter, the organic layer was concentrated under reduced pressure after filtering out the drying agent. The resulting concentrated residue was purified by fractionation silica gel chromatography (solvent: chloroform/methanol=40/1). As a result, Compound 11 (91.0 mg, 75% yield) in the form of a white solid was obtained.

An ESI-MS (positive) measurement was conducted on the Compound 11. The measurement showed that the m/z was 1085.5 [(M+H)$^+$]. Also, the result of $^1$H-NMR (400 MHz, CD$_3$Cl) measurement found that δ=9.01 (3H,bs), 7.67 (3H, s), 7.31 (1H, bs), 7.27-7.00 (12H, m), 3.71 (2H, bs), 3.64-3.39 (1H, m), 3.12-2.99 (2H, m), 2.33 (1H, m), 2.32 (6H, m), 2.20 (2H, m), 2.04 (6H, m), 1.82-1.73 (1H, m), 1.62-1.47 (4H, m), 1.47 (27H, s), 1.39-1.25 (2H, m). From this, a structure of the Compound 11 was confirmed.

Compound 12 was obtained by the following procedure. First, trimethylsilyl chloride (0.25 mL, 2.64 mmol) was dissolved in 0.49 mL of dichloromethane, and a phenol solution obtained by dissolving phenol (549 mg, 5.83 mmol)

in 1.46 mL of dichloromethane was added. After stirring, Compound 11 (34.7 mg, 32.6 μmol) was added, and the mixture was stirred for 1.5 hours at room temperature in a shade to obtain a solution of Compound 11 as the product of reaction. Thereafter, chloroform was added to the reaction solution of Compound 11, and the organic layer was washed by a saturated aqueous solution of sodium hydrogen carbonate to form a yellow solid precipitate. The yellow solid was dissolved in acetic acid and then cooled down to 4° C. The resulting coagulated solid was filtered out to obtain Compound 12 (7.9 mg, 32% yield).

An ESI-MS (positive) measurement was conducted on Compound 12. The measurement showed that the m/z was 763.6 [(M+H)$^+$]. Also, the result of $^1$H-NMR (400 MHz, d$_6$DMSO) measurement found that δ=9.57 (3H, s), 7.97 (1H, m), 6.87 (6H, m), 6.67 (3H, d, J=7.7 Hz), 6.21 (3H, d, J=7.7 Hz), 4.98 (6H, bs), 3.67 (2H, d, J=5.1 Hz), 3.56 (1H, m), 3.16-3.04 (2H, m), 2.36 (1H, m), 2.25 (6H, m), 2.19-2.07 (2H, m), 1.93 (6H, m), 1.83 (1H, m), 1.50 (4H, m), 1.33 (2H, m). From this, a structure of the Compound 12 was confirmed.

EXAMPLE 2

Synthesis of a Ligand

By using the Linker Compound 12 obtained in Example 1, a ligand having a structure represented by general formula (4) was obtained by the procedure described below, wherein, in general formula (4), $m^1$, $m^2$, and $m^3$ are 2, and n is 1.

As shown in general formula (14) below, the Linker Compound 12 obtained in Example 1, and the Compound 13 (5 equiv.) serving as a sugar molecule represented by general formula (10) were dissolved in a mixed solvent of H$_2$O/dimethylacetoamide (DMAc in the formula)/acetic acid (AcOH)=5/20/1 to form a Schiff base at a pH of 3 to 4 at 37° C. Then, the content of the solvent was changed to H$_2$O/DMAc/AcOH=20/5/24, and NaBH$_3$CN (30 equiv.) was added at a pH of 3 to 4 at 37° C. to cause a reductive amination reaction. Thereafter, the resulting compound was purified by gel filtration chromatography with Sephadex G-50 (manufactured by Amersham Biosystems Co., Ltd.) and was desalted. As a result, Compound 14 was obtained as as a ligand including three units of sugar molecules.

Specifically, Compound 14 was obtained by the following procedure. The Linker Compound 12 (0.5 mg, 655 nmol) obtained in Example 1 and Compound 13 (2.8 mg, 3 μmol) were dissolved in a mixed solvent containing water (25 μL), dimethylacetoamide (100 μL), and acetic acid (5 μL). The resulting mixture was heated overnight at 37° C. in a sealed tube to obtain a solution of Linker Compound 12 and Compound 13 as the product of reaction. The reaction solution of Linker Compound 12 and Compound 13 was mixed with an NaBH$_3$CN solution obtained by dissolving NaBH$_3$CN (2.7 mg, 39.2 μmol) in 20 μL of acetic acid, heated for 3 days at 37° C., concentrated under reduced pressure, and subjected to gel filtration chromatography with Sephadex G-50 (solvent: PBS containing 0.3 M of NaCl). The resulting target fraction was concentrated under reduced pressure, and the resulting concentrated residue was desalted with Sephadex G-25 (solvent: water). The desalted target fraction was concentrated under reduced pressure, dissolved in water, and freeze-dried. As a result, Compound 14 (1.5 mg, 66% yield) in the form of a white powder was obtained.

A mass of Compound 14 to be obtained is 3291.28 Da (Dalton). Compound 14 shown in general formula (14) was observed as a trivalent ion [M−12Na+9H]$^{3-}$ at the peak of m/z 1008.19 obtained by a time-of-flight mass spetrometer measurement. Also, the result of $^1$H-NMR (500 MHz, D$_2$O) measurement found that δ=7.20 (3H, m), 6.82 (6H, m), 6.64 (3H, m), 5.35 (3H, d, J=3.5 Hz), 5.13 (3H, J=2.5 Hz), 4.51 (3H, d, J=2.4 Hz), 4.29 (6H, m), 4.18 (6H, m), 4.06 (6H, m), 3.97 (9H, m), 3.87 (3H, m), 3.82 (3H, m), 3.78 (6H, m), 3.68 (9H, m), 3.56 (9H, s), 3.34 (6H, m), 3.24 (3H, dd, J=3.4, 10.5 Hz), 3.08 (4H, m), 2.44 (6H, m), 2.33 (1H, m), 2.27 (2H, t), 1.86 (1H, m), 1.56-1.46 (2H, m), 1.35-1.14 (4H, m). From this, a structure of the Compound 14 was confirmed.

EXAMPLE 3

Synthesis of a Linker Compound

A linker compound of the present invention, having a structure represented by general formula (1), where n is 1, and X has a structure represented by general formula (3), where $m^4$, $m^5$, $m^6$, and $m^7$ are all 2, and $p^1$ and $p^2$ are 1, was synthesized according to the procedure described below.

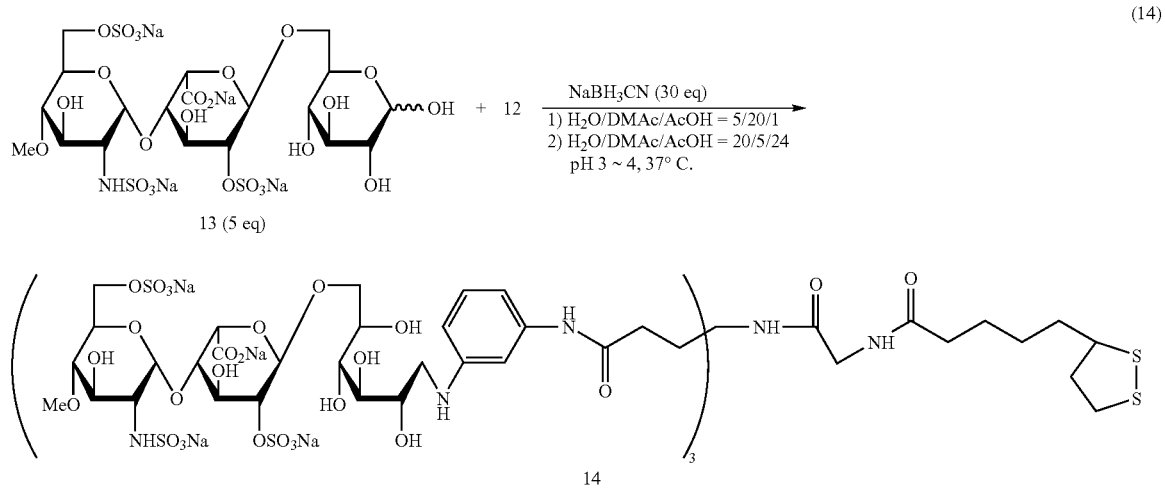

(14)

As shown in general formula (15) below, a trifluoroboron ether adduct ($BF_3 \cdot OEt_2$ in the formula) was added to MeOH, and refluxed under acidic conditions. Then, dicarboxylic acid (Compound 15) was esterified to obtain an ester derivative (Compound 16) at a 79% yield.

Thereafter, Z-glycine (1.1 equiv.) was condensed with Compound 16 in the presence of HOBt (1.1 equiv.) and dicyclohexyl carbodiimide (DCC in the formula) in $CH_2Cl_2$. As a result, a glycine derivative (Compound 17) was obtained at the yield of 94%.

Then, 2N NaOH was added to MeOH, and the ester group of the Compound 17 was hydrolyzed under alkaline conditions. As a result, a dicarboxylic acid derivative (Compound 18) was obtained at the yield of 98%.

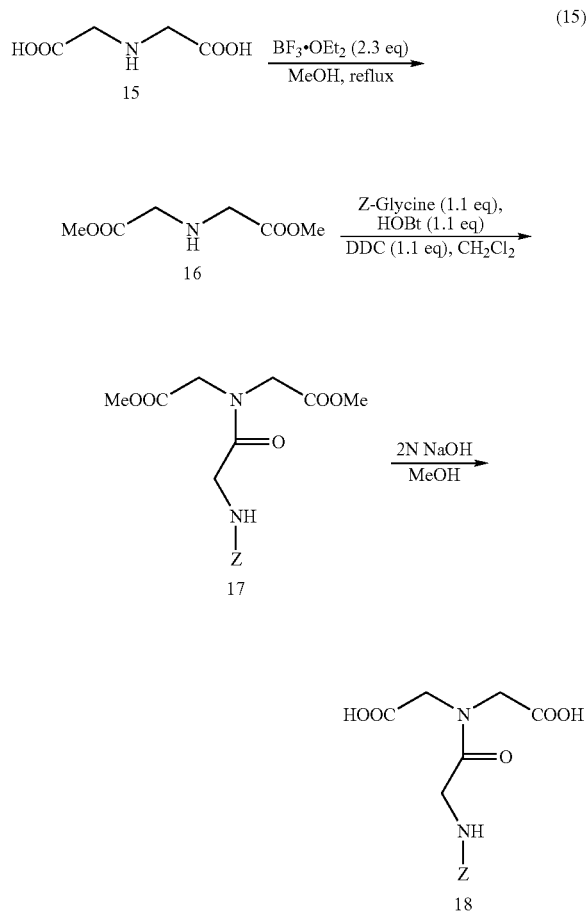

(15)

Specifically, the Compounds 16 to 19 were obtained by the procedures described below.

That is, Compound 16 was obtained by the following procedure. First, Compound 15 (iminodiacetic acid; 10.0 g, 75.1 mmol) and $BF_3 \cdot OEt_2$ (boron trifluoride-diethyl ether complex; 22 mL, 173 mmol) were dissolved in 50 mL of anhydrous methanol. The mixture was refluxed for 5 hours under argon atmosphere, neutralized by adding a saturated aqueous solution of sodium hydrogen carbonate, and extracted with chloroform. To the water layer, triethylamine was added until the pH reached 9. Then, the layer was extracted with chloroform, dried using sodium sulfate anhydride as a drying agent, and concentrated under reduced pressure after filtering out the drying agent. As a result, Compound 16 (9.61 g, 79% yield) in the form of a yellow oily matter was obtained.

An ESI-MS (positive) measurement was conducted on the Compound 16. The measurement showed that the m/z was 162.1 [(M+H)$^+$]. Also, the result of $^1$H-NMR (400 MHz, $CD_3Cl$) measurement found that δ=3.74 (6H, s), 3.48 (4H, s), 2.00 (1H, s). From this, a structure of the Compound 16 was confirmed.

Compound 17 was obtained by the following procedure. First, Compound 16 (1.00 g, 6.21 mmol), dicyclohexyl carbodiimide (1.41 g, 6.83 mmol), and HOBt (0.92 g, 6.83 mmol) were dissolved in 25 mL of anhydrous dichloromethane. The resulting mixture was stirred for half an hour at 0° C. under argon atmosphere, and for 5 days with Z-glycine (1.42 g, 6.83 mmol) at room temperature. The precipitate formed by the stirring was filtered out, and the filtrate was extracted with chloroform. The organic layer was washed twice in each of 1N HCl and a saturated aqueous solution of sodium hydrogen carbonate, and further washed once by water. The organic layer was dried using sodium sulfate anhydride as a drying agent, and was concentrated under reduced pressure after filtering out the drying agent. The resulting concentrated residue was purified by fractionation silica gel chromatography (solvent: chloroform/acetone=2/1). As a result, Compound 17 (2.05 g, 94% yield) in the form of a white solid was obtained.

An ESI-MS (positive) measurement was conducted on Compound 17. The measurement showed that the m/z was 375.1 [(M+Na)$^+$]. Also, the result of $^1$H-NMR (400 MHz, $CD_3Cl$) fount that δ=7.36 (5H, m), 5.69 (1H, bst), 5.12 (2H, s), 4.22, 4.12 (4H, s, s), 4.06 (2H, d), 3.78, 3.73 (4H, s, s). From this, a structure of the Compound 17 was confirmed.

Compound 18 was obtained by the following procedure. First, Compound 17 (1.50 g, 4.26 mmol) was dissolved in 20 mL of methanol, and 2N NaOH (9 mL) was added. The mixture was stirred for 2.5 hours at 0° C., neutralized by adding Dowex 50WX-8 (H$^+$ form) until the pH reached 6, and concentrated under reduced pressure after filtering out the Dowex 50WX-8. The resulting concentrated residue was concentrated under reduced pressure after adding water and filtering out an insoluble matter, and freeze-dried. As a result, Compound 18 (1.30 g, 98% yield) in the form of a white solid was obtained.

An ESI-MS (negative) measurement was conducted on the Compound 18. The measurement showed that the m/z was 321.1 [(M−2H+Na)$^-$]. Also, the result of $^1$H-NMR (400 MHz, $d_6$-DMSO) measurement found that δ=7.32 (5H, m), 7.21 (1H, m), 5.01 (2H, s), 3.93, 3.84 (4H, s, s), 3.72 (2H, d, J=5.4 Hz). From this, a structure of the Compound 18 was confirmed.

Thereafter, as shown in general formula (16) below, Compound 19 (2.5 equiv.) whose aromatic amino group ends are protected by the Boc group was allowed to react with Compound 18 in the presence of FDPP (2.5 equiv.) and DIPEA (2.5 equiv.) in DMF. As a result, an N-Boc amine derivative (Compound 20) was obtained at the yield of 60%.

Then, a catalytic hydrogen reduction was performed in MeOH in the presence of Pd/C to deprotect the Z group of the Z-glycine that underwent the condensation reaction with the Compound 20. As a result, an amine derivative (Compound 21) was obtained at the yield of 92%.

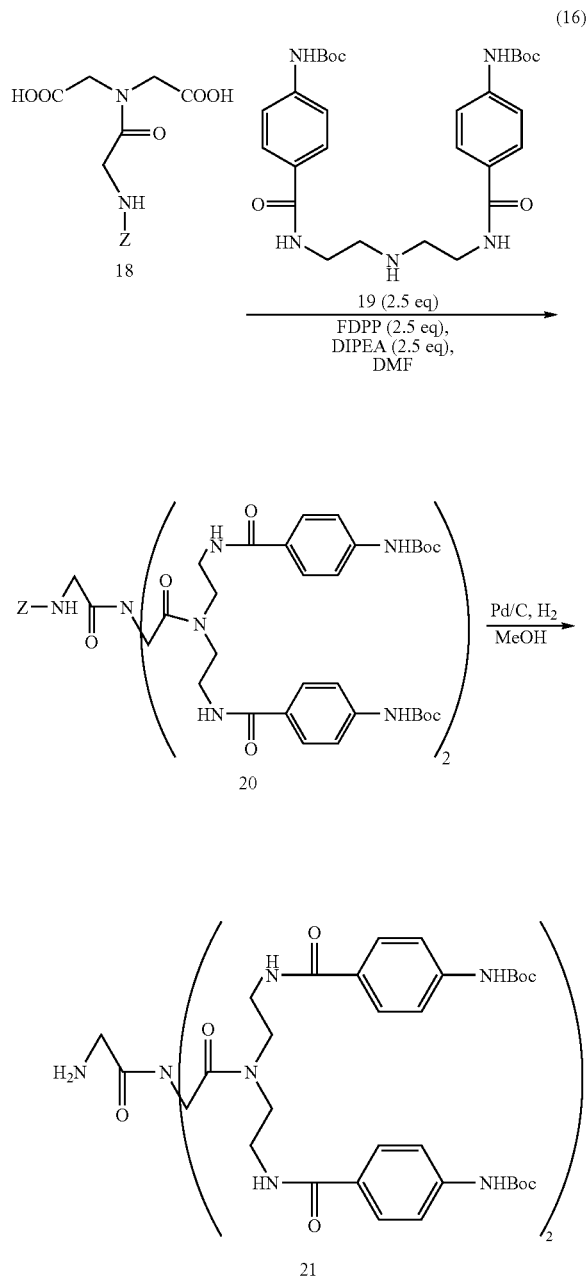

Specifically, Compounds 19 to 21 were obtained by the procedures described below.

Compound 19 was obtained by the following procedure. First, 4-aminobenzoic acid (3.33 g, 14.0 mmol) and HOBt (1.93 g, 14.3 mmol) were suspended in 60 mL of anhydrous dichloromethane, and the mixture was stirred for 15 minutes at 0° C. under argon atmosphere. Then, a WSCI.HCl solution obtained by dissolving WSCI.HCl (2.87 g, 15.0 mmol) in 30 mL of anhydrous dichloromethane was added, and the mixture was stirred for 50 minutes to obtain a solution of 4-aminobenzoic acid and HOBt as the product of reaction. To the solution of 4-aminobenzoic acid and HOBt reaction solution, diethylenetriamine (0.79 mL, 7.00 mmol) was added, and the mixture was stirred overnight at room temperature in a shade to obtain a white crystal. The white crystal was filtered out, and recrystallized from methanol. As a result, Compound 19 (3.53 g, 92.9% yield) in the form of a white crystal was obtained.

An ESI-MS (positive) measurement was conducted on Compound 19. The measurement showed that the m/z was 542.4 [(M+H)$^+$]. Also, the result of $^1$H-NMR (400 MHz, CD$_3$Cl) found that δ=7.77-7.74 (4H, d, J=8.7 Hz), 7.50-7.48 (4H, d, J=8.6 Hz), 3.70-3.66 (4H, m, J=5.2 Hz), 3.34-3.28 (4H, m, J=5.6 Hz), 1.53 (18H, s). From this, a structure of the Compound 19 was confirmed.

Compound 20 was obtained by the following procedure. First, Compound 18 (50.0 g, 154 μmol), Compound 19 (209 mg, 386 μmol), and FDPP (148 mg, 386 μmol) were dissolved in 30 mL of dimethylformamide anhydride. To the resulting mixture, diisopropyl ethylamine (67.2 μL, 386 μmol) was added, and the mixture was stirred for 20 hours at room temperature under argon atmosphere to obtain a solution of Compound 18 and Compound 19 as the product of reaction. The reaction solution of Compound 18 and Compound 19 was concentrated under reduce pressure, and the resulting concentrated residue was extracted with chloroform. The organic layer was washed by 10% citric acid and a saturated aqueous solution of sodium hydrogen carbonate, dried using sodium sulfate anhydride as a drying agent, and concentrated under reduced pressure after filtering out the drying agent. The concentrated residue was purified by fractionation silica gel chromatography (solvent: chloroform/methanol=10/1). As a result, Compound 20 (125 mg, 59% yield) in the form of a white solid was obtained.

An ESI-MS (positive) measurement was conducted on Compound 20. The measurement showed that the m/z was 1393.7 [(M+Na)$^+$]. Also, the result of $^1$H-NMR (400 MHz, CDCl$_3$) measurement found that δ=7.88 (1H, bs), 7.73-7.66 (10H, m), 7.56 (1H, bs), 7.38 (4H, d, J=8.4 Hz), 7.34-7.29 (6H, m), 7.17, 7.05 (2H, bs, bs), 5.35 (1H, bs), 5.00 (2H, s), 3.96 (2H, bs), 3.64 (4H, band), 3.55 (4H, band), 3.51 (6H, band), 3.43, 3.27, 3.17 (6H, bs, bs, bs), 1.50, 1.49 (36H, s, s). From this, a structure of the Compound 20 was confirmed.

Compound 21 was obtained by the following procedure. First, Compound 20 (103 mg, 74.4 μmol) was dissolved in 3 mL of methanol, and 10% Pd/C (84 mg) was added. The mixture was stirred for 47 hours at room temperature in hydrogen atmosphere, and was concentrated under reduced pressure after filtering out the Pd/C. As a result, Compound 21 (84.9 mg, 92% yield) in the form of a white solid was obtained.

An ESI-MS (positive) measurement was conducted on Compound 21. The measurement showed that the m/z was 630.3 [(M+H+Na)$^{2+}$]. From this, a structure of the Compound 21 was confirmed.

Moreover, as shown in general formula (17) below, Compound 21 was condensed with thioctic acid (Compound 10; 1.1 equiv.) in a mixed solvent of CH$_2$Cl$_2$/DMF=4/1 and in the presence of HOBt (1.1 equiv.) and WSCI.HCl (1.0 equiv.). As a result, an amide compound (Compound 22) was obtained at the yield of 75%.

Furthermore, the Boc groups of the Compound 22 so obtained were deprotected in CH$_2$Cl$_2$ under acidic conditions containing TFA. As a result, Compound 23 (91% yield) was obtained as a linker compound including four hydrocarbon derivative chains each having an aromatic amino group.

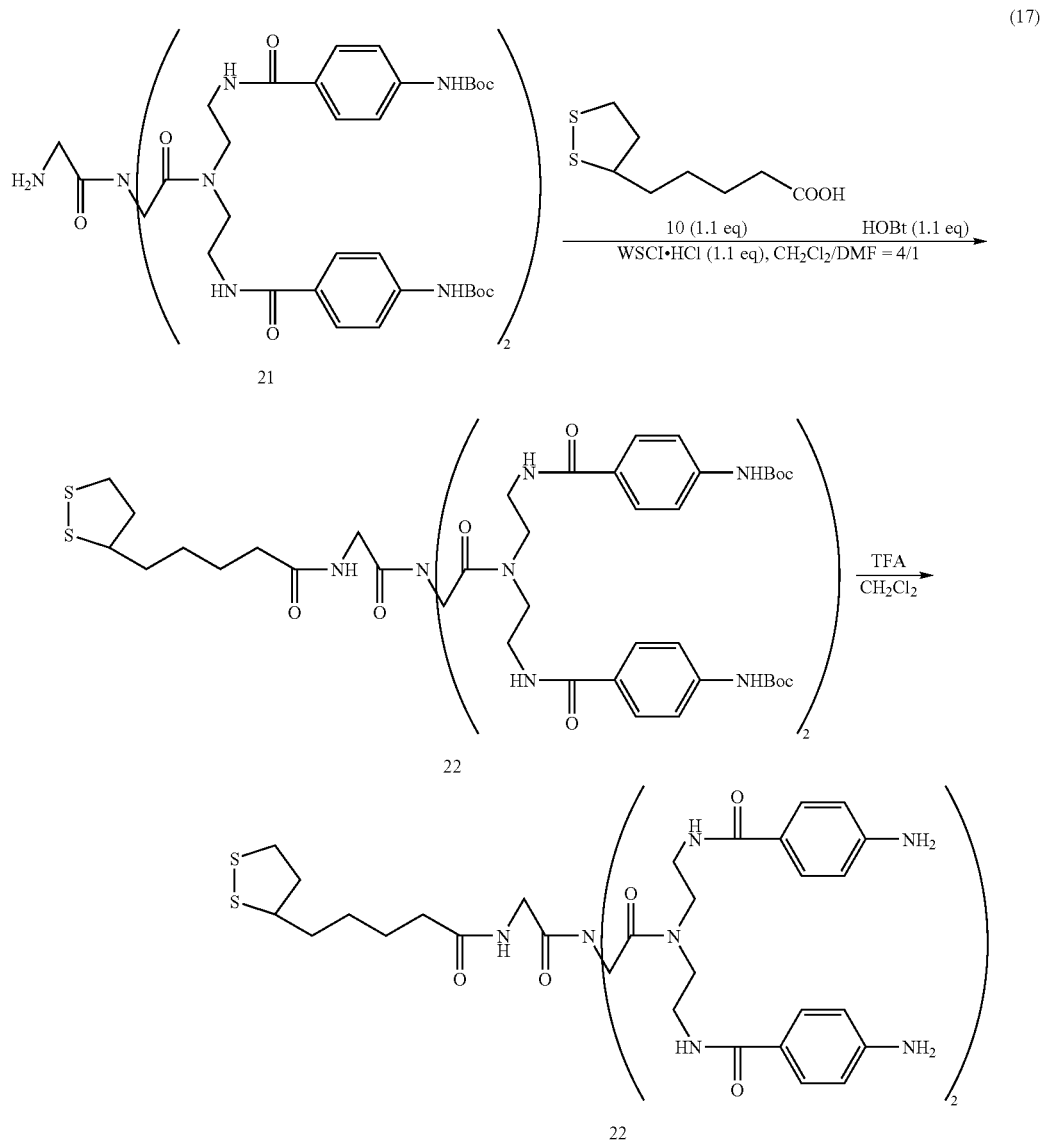

(17)

Specifically, the Compounds 22 and 23 were obtained by the procedures described below.

Compound 22 was obtained by the following procedure. First, Compound 10 (12.8 g, 62.2 μmol) and HOBt (8.4 mg, 62.2 μmol) were dissolved in 10 mL of anhydrous dichloromethane. The resulting mixture was stirred at 0° C. in a shade under argon atmosphere to obtain a solution of Compound 10 and HOBt as the product of reaction. Thereafter, Compound 21 (70.0 mg, 56.5 μmol) was dissolved in 0.5 mL of dimethylformamide, and the mixture was added dropwise into the reaction solution of Compound 10 and HOBt. The resulting mixture was stirred for 19 hours at room temperature, and was extracted with ethyl acetate to obtain an extract. The organic layer of the extract was washed once in each of a 10% aqueous solution of citric acid and a saturated aqueous solution of sodium hydrogen carbonate. The organic layer was dried using sodium sulfate anhydride as a drying agent, and was concentrated under reduced pressure after filtering out the drying agent. The resulting concentrated residue was purified by fractionation silica gel chromatography (solvent: chloroform/methanol=15/1). As a result, Compound 22 (60.8 mg, 75% yield) in the form of a white solid was obtained.

An ESI-MS (positive) measurement was conducted on Compound 22. The measurement showed that the m/z was 735.3 [(M+2Na)$^{2+}$]. Also, the result of $^1$H-NMR (400 MHz, CDCl$_3$) measurement found that δ=7.76-7.79 (11H, m), 7.55 (1H, bs), 7.42 (4H, d, J=8.6 Hz), 7.35 (5H, m), 7.13, 7.00, 6.97 (3H, bs, bs, bs), 5.84 (1H, bs), 4.04 (2H, bs), 3.67 (4H, band), 3.55 (4H, band), 3.48 (8H, band), 3.41, 3.29, 3.22 (6H, bs, bs, bs), 3.16-3.03 (2H, m), 2.39 (1H, m), 2.02 (1H, m), 1.84 (1H, m), 1.58-1.52 (4H, m), 1.51, 1.49 (36H, s, s), 1.35 (2H, m). From this, a structure of the Compound 22 was confirmed.

Compound 23 was obtained by the following procedure. First, Compound 22 (48.2 mg, 33.8 μmol) was dissolved in 1 mL of dichloromethane, and 2 mL of trifluoroacetic acid was added. The mixture was stirred for one hour at 0° C. in a shade, and then concentrated under reduced pressure. The resulting residue was dissolved in methanol, neutralized by adding Dowex Marathon A (OH⁻ from), and concentrated under reduced pressure after filtering out the Dowex Marathon A. As a result, Compound 23 (31.6 mg, 91% yield) in the form of a white solid was obtained.

An ESI-MS (positive) measurement was conducted on the Compound 23. The measurement showed that the m/z was 534.2 [(M+2Na)$^{2+}$]. From this, a structure of the Compound 23 was confirmed.

EXAMPLE 4

Synthesis of a Ligand

By using the Linker Compound 23 obtained in Example 3, a ligand having a structure represented by general formula (5) was obtained by the procedure described below wherein, in general formula (5), $m^4$, $m^5$, $m^6$, and $m^7$ are all 2, and n is 1, and $p^1$ and $p^2$ are 1.

As shown in general formula (18) below, the Linker Compound 23 obtained in Example 3, and Compound 13 (5 equiv.) serving as a sugar molecule represented by general formula (18) below were dissolved in a mixed solvent of $H_2O/DMAc/AcOH=5/20/1$ to form a Schiff base (imine form in the formula) at a pH of 3 to 4 at 37° C. Thereafter, the content of the solvent was changed to $H_2O/DMAc/AcOH=9/20/22$, and NaBH$_3$CN (64 equiv.) was added to perform a reduction reaction (reduction in the formula) at a pH of 3 to 4 at 37° C. Thereafter, the resulting compound was purified by gel filtration chromatography with Sephadex G-50 and desalted. As a result, Compound 24 was obtained as a ligand including four units of sugar molecules.

Specifically, Compound 24 was obtained by the following procedure. The linker compound 23 (0.5 mg, 488 nmol) and Compound 13 (2.1 mg, 2.4 µmol) were dissolved in a mixed solvent containing water (25 µL), dimethylacetoamide (100 µL), and acetic acid (5 µL). The mixture was heated for 3 hours at 37° C. in a sealed tube to obtain a solution of Linker Compound 23 and Compound 13 as the product of reaction. To the reaction solution of Linker Compound 23 and Compound 13, a solution obtained by dissolving acetic acid (45 µL) in NaH$_3$CN (2.18 mg, 31.2 µmol) was added, and the mixture was heated for 3 days at 37° C. The resulting mixture was concentrated under reduced pressure and then purified with Sephadex G-50 (1.6×80 cm, PBS-0.3 NaCl). The resulting target fraction was concentrated under reduced pressure, and the resulting concentrated residue was desalted with Sephadex G-25 (1.6×40 cm, water). The resulting target fraction was concentrated under reduced pressure, dissolved in water, and then freeze-dried. As a result, Compound 24 (1.0 mg, 47% yield) in the form of a white solid was obtained.

A mass of Compound 24 to be obtained is 4369.37 Da (Dalton). Compound 24 shown in general formula (18) was observed as a trivalent ion [M-13Na+10H]$^{3-}$ at the peak of m/z 1368.93 obtained by time-of-flight mass spetrometer measurement. Also, the result of NMR spectrum measurement found that δ=7.70-7.55 (8H, m), 6.78-6.64 (8H, m), 5.34 (4H, s), 5.20 (8H, d, J=3.3 Hz), 5.15 (4H, bs), 4.52 (4H, bs), 4.29 (8H, m), 4.19 (8H, m), 4.05 (4H, m), 3.99 (4H, band), 3.87-3.80 (16H, band), 3.73-3.66 (24H, m), 3.87 (3H, m), 3.57 (12H, s), 3.49 (4H, dd, J=3.8, 9.7), 3.39-3.34 (14H, m), 3.26-3.19 (12H, m), 2.60 (1H, m), 2.21-2.13 (2H, m), 1.77 (1H, m), 1.50-1.13 (4H, m). From this, a structure of the Compound 24 was confirmed.

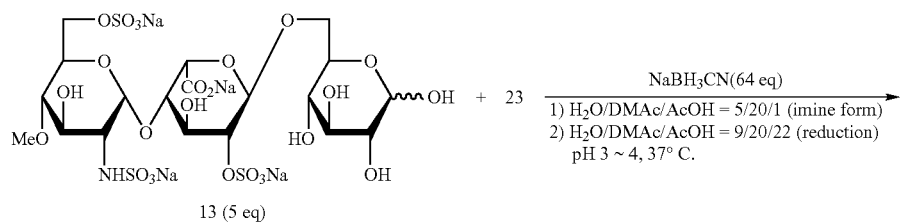

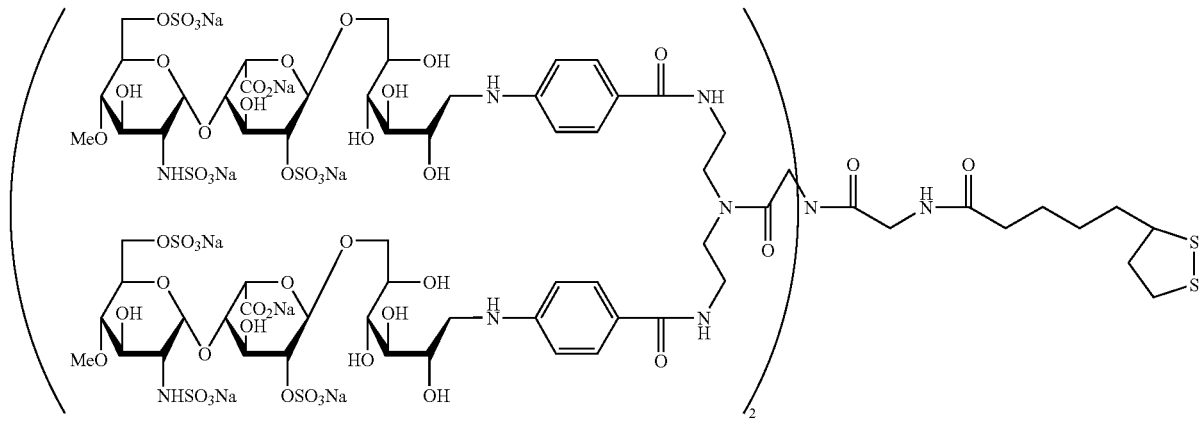

EXAMPLE 5

An SPR Measurement Using a Ligand Compound

An SPR measurement was performed using Compound 14, obtained in Example 2, which is a ligand having a structure represented by general formula (4), where $m^1$, $m^2$, and $m^3$ are all 2, and n is 1.

That is, by the procedure described below, a ligand (Compound 14) was immobilized on a surface of a glass substrate with a thin gold film deposited thereon, and the binding behavior of Compound 14 with a recombinant von Willebrand's Factor (hereinafter abbreviated to rvWF), which is a heparin binding protein, was observed.

(5-1 Preparation of a Ligand-Introduced Chip)

First, a sensor chip (manufactured by Japan Laser Electronics Co., Ltd.), prepared by depositing a gold film of 50 nm thick on a glass substrate of 13 mm×20 mm×0.7 mm, was placed in a UV ozone washer (product name: NL-UV253, Japan Laser Electronics Co., Ltd.), and was exposed to ultraviolet rays for 20 minutes so as to wash the gold surface of the sensor chip with ozone. Subsequently, the sensor chip was mounted on a Teflon™ cell holder in a cell. The cell, to which 50 μL of a methanol solution containing 0.1 mM of Compound 14 was added, was sealed and then gently shaken overnight at room temperature with a Bio Dancer (product name, New Brunswick Scientific Co., Ltd.). Thereafter, the cell was washed six times with 100 μL of methanol, and the sensor chip was removed from the Teflon™ cell holder. The removed sensor chip was then immersed in a Petri dish full of methanol and washed twice by gently shaking the Petri dish. Thereafter, the sensor chip was washed with water and methanol in this order in the same manner as described above, so as to obtain a ligand-introduced chip (ligand carrier). The ligand carrier was air-dried and then mounted on a sensor chip cartridge (glass prism) of a surface plasmon resonance apparatus SPR670 (product name, Japan Laser Electronics Co., Ltd.).

(5-2 Examination of Nonspecific Interaction Due to a Hydrophobic Interaction Between a Ligand-Introduced Chip and a Protein)

A phosphate buffer solution (PBS; pH 7.4) serving as a running buffer was flown onto the ligand-introduced chip at a flow rate of 15 μL/min at 25° C. until a resonant angle change measured by the surface plasmon resonance apparatus became constant. Thereafter, bovine serum albumin (BSA) serving as a protein used for an SPR measurement was dissolved in the running buffer so as to prepare a BSA solution with a BSA concentration of 1 mg/mL. Then, 60 μL solution was flown onto the surface of the ligand-introduced chip at a flow rate of 15 μL/min.

In order to examine a nonspecific interaction based on a hydrophobic interaction between the gold formed on the surface of the ligand-introduced chip on which the BSA solution was flown, and the BSA serving as a protein, a measurement was conducted using the surface plasmon resonance apparatus. The measurement found almost no resonant angle change. It is inferred herefrom that a binding interaction between the protein and the sugar can be quantitatively evaluated because the ligand-introduced chip including the Compound 14 introduced thereon reduces the influence of a nonspecific interaction between the protein and ligand-introduced chip.

(5-3 Analysis of a Dissociation Constant of rvWF)

Except that an rvWF solution was used instead of the BSA solution (5-2) injected onto the ligand-introduced chip (obtained in 5-1), the same procedure as in (5-2) was carried out to inject the rvWF solution onto the surface of the ligand-introduced chip. It is to be noted that rvWF was dissolved in the running buffer so as to prepare an rvWF solution with a concentration of 125 nM to 1600 nM.

The rvWF solution was injected onto the surface of the ligand-introduced chip at varying concentrations, and a response (RU; response unit) based on bonding between Compound 14 and rvWF was measured as a function of injection time (sec) of the rvWF solution using the surface plasmon resonance apparatus. The result is shown in FIG. 1.

It is to be noted that in order to reuse the ligand-introduced chip with the rvWF, 10 mM NaOH was flown onto the surface of the ligand-introduced chip for one minute or more at a flow rate of 60 μL/min.

In addition, a dissociation constant ($K_D$), a binding rate constant ($k_a$), and a dissociation rate constant ($k_d$) were calculated, using software attached to the surface plasmon resonance apparatus (SPR670), based on a result (FIG. 1) yielded by observing the binding behavior of Compound 14 (ligand) with rvWF. The result is shown in Table 1.

TABLE 1

| Ligand | Compound 14 | Compound 25 |
| --- | --- | --- |
| Dissociation constant $K_D$ (M) | $1.2 \times 10^{-6}$ | $2.6 \times 10^{-6}$ |
| Binding rate constant $k_a$ (M$^{-1}$sec) | $6.60 \times 10^3$ | $8.38 \times 10^3$ |
| Dissociation rate constant $k_d$ (sec$^{-1}$) | $8.05 \times 10^{-3}$ | $2.19 \times 10^{-2}$ |

COMPARATIVE EXAMPLE

A procedure described in Document 1 was followed to prepare Compound 25, i.e., a ligand with a structure represented by the following general formula (19), including one unit of oligosaccharide having a structure represented by general formula (10).

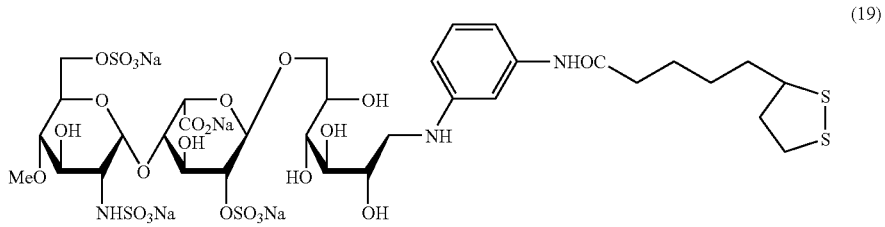

(19)

Then, except that the Compound 25 was used instead of the Compound 14, the procedure in (5-1) of Example 5 was followed to obtain a ligand-introduced chip. According to the procedure in (5-2) of Example 5, in was confirmed that there was no nonspecific interaction based on a hydrophobic interaction between the ligand-introduced chip and the protein. Thereafter, according the procedure in (5-3) of Example 5, the rvWF solution was injected onto the surface of the ligand-introduced chip, and changes in resonance angle as a function of injection time of the rvWF solution was measured using the surface plasmon resonance apparatus, so as to examine the binding behavior of Compound 25 with rvWF. The result is shown in FIG. 2.

Figure 2:
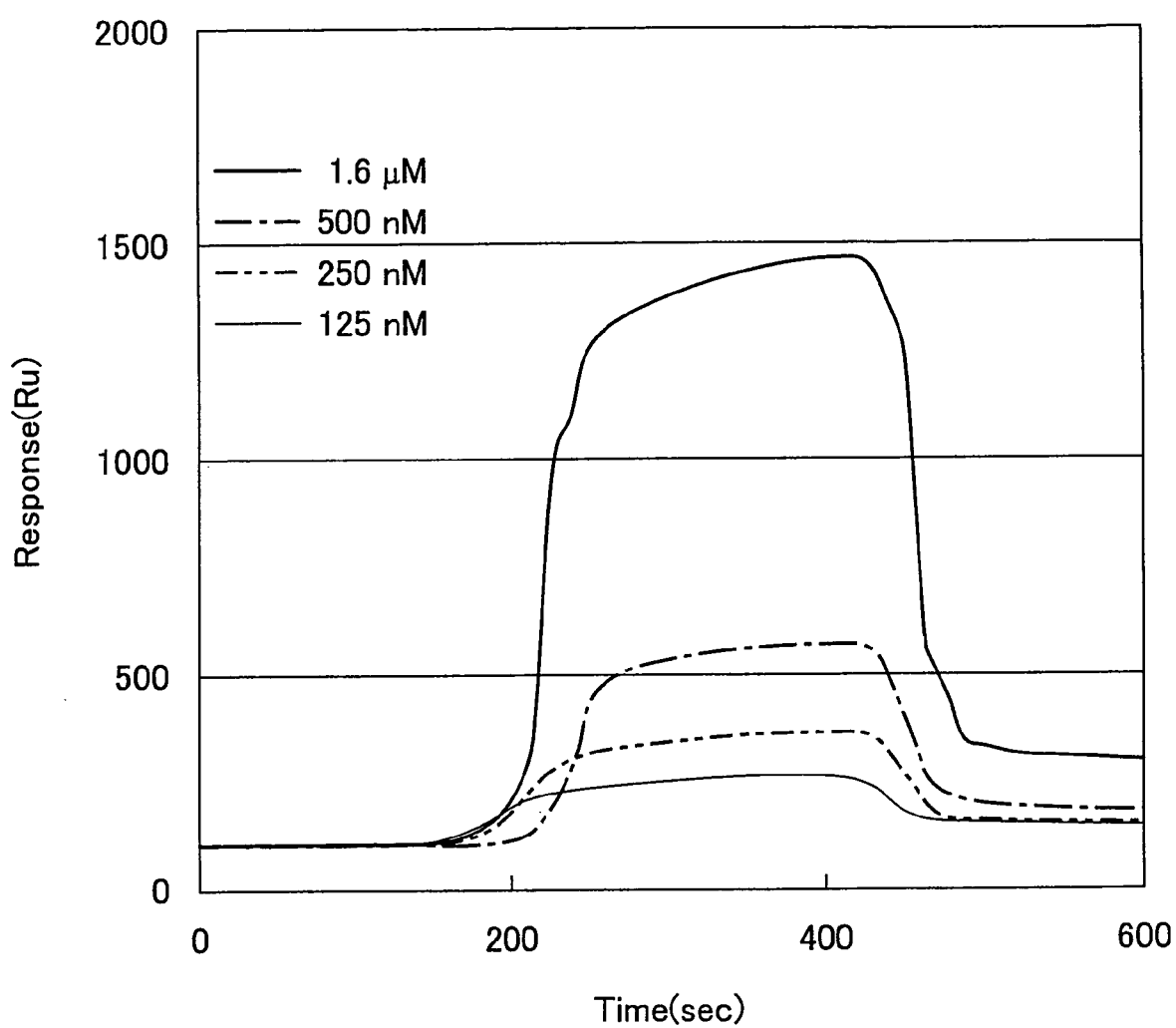
FIG. 2 is a graph showing a result of an SPR measurement measuring the bonding between a ligand-introduced chip, on which a conventional ligand is immobilized, and rvWF.

In addition, a dissociation constant ($K_D$), a binding rate constant ($k_a$), and a dissociation rate constant ($k_d$) were calculated, based on FIG. 2, according to the procedure in (5-3) of Example 5. The result is shown in Table 1.

It can be seen from Table 1 that the ligand-introduced chip using Compound 14, i.e., the ligand of the present Example has a higher affinity for rvWF than the ligand-introduced chip using Compound 25. Thus, with the ligand-introduced chip of the present Example, biological activities of sugar molecules can be observed with high reproducibility. The ligand-introduced chip is therefore highly suitable for revealing structures of sugar molecules and/or evaluating biological activities of sugar molecules.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, the present invention provides a linker compound capable of two-dimensionally arranging three or four units of sugar molecules with high reproducibility on a protein-analyzing supporter or the like. With the linker compound, the influence of a nonspecific interaction with a protein cari be ignored almost completely.

In addition, a ligand of the present invention includes the linker compound with a sugar molecule introduced thereinto. With the ligand, three or four units of sugar molecules can be collected, thereby making it possible to observe biological activities of sugar molecules with high reproducibility.

Therefore, the present invention, using the linker compound and ligand, can be applied to the biotechnology industry to detect interactions of biomolecules. The present invention is particularly useful in fields where chip technology and an affinity column are used. The present invention is also useful in fields where a bioprobe and a biosensor are used. Other applicable fields of the invention include the pharmaceutical industry, and medical technology for diagnosis and inspections.

The invention claimed is:

1. A linker compound comprising:
a structure represented by following general formula (1):

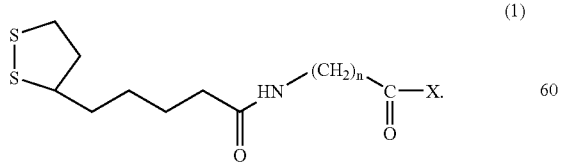

where n is an integer of 1 to 6, and
X has a structure represented by the following general formula (2):

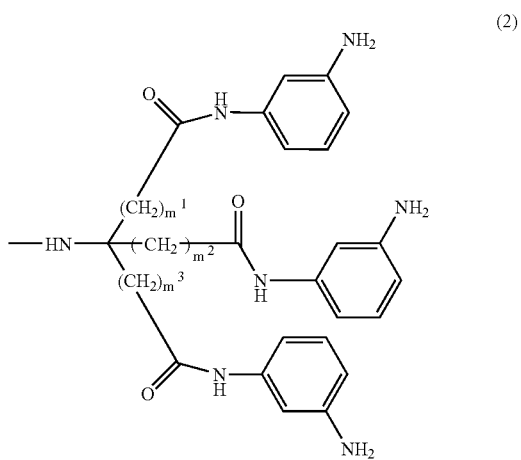

where $m^1$, $m^2$ and $m^3$ are independently an integer of 1 to 6.

2. The linker compound according to claim 1, wherein $m^1$, $m^2$, and $m^3$ are all 2 in said general formula (2).

3. A linker compound comprising:
a structure represented by following general formula (1):

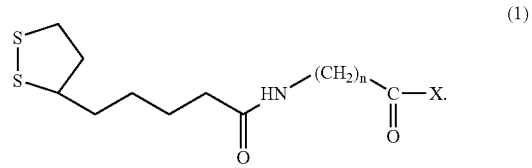

where n is an integer of 1 to 6, and
X has a structure represented by following formula (3):

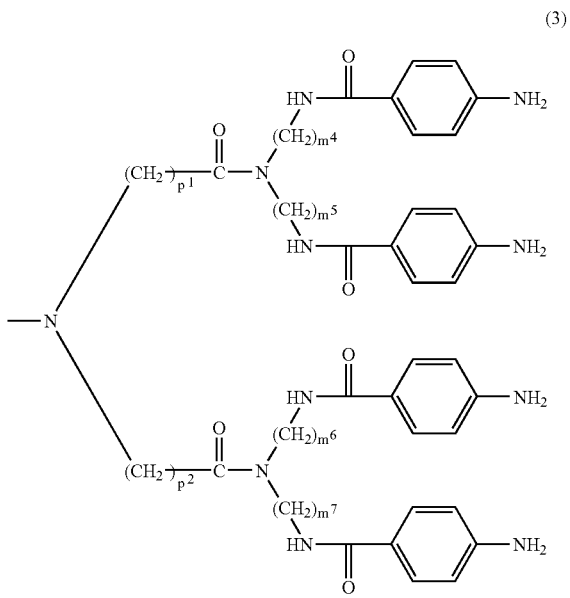

where $m^4$, $m^5$, $m^6$, $m^7$, $p^1$, and $p^2$ are independently an integer of 1 to 6.

4. The linker compound according to claim 3, wherein $m^4$, $m^5$, $m^6$, and $m^7$ are all 2 and $p^1$ and $p^2$ are both 1 in the general formula (3).

5. A ligand which comprises the aromatic amino group of the linker compound according to claim 1, and a sugar molecule introduced into the aromatic amino group.

6. The ligand according to claim 5, wherein the sugar molecule is at least one kind of sugar selected from the group consisting of a monosaccharide, an oligosaccharide, and a polysaccharide.

7. A ligand of a structure represented by following general formula (4):

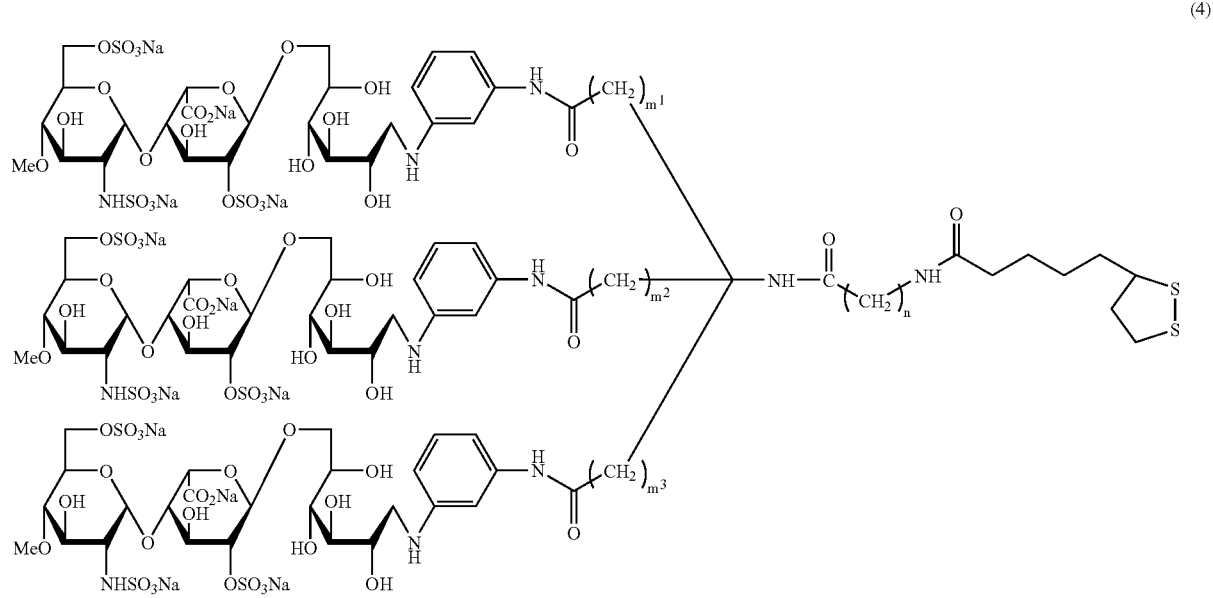

(4)

wherein $m^1$, $m^2$, $m^3$, and n are independently an integer of 1 to 6.

8. The ligand according to claim 7, wherein $m^1$, $m^2$, and $m^3$ are all 2 and n is 1 in the general formula (4).

9. A ligand comprising a structure represented by following formula (5):

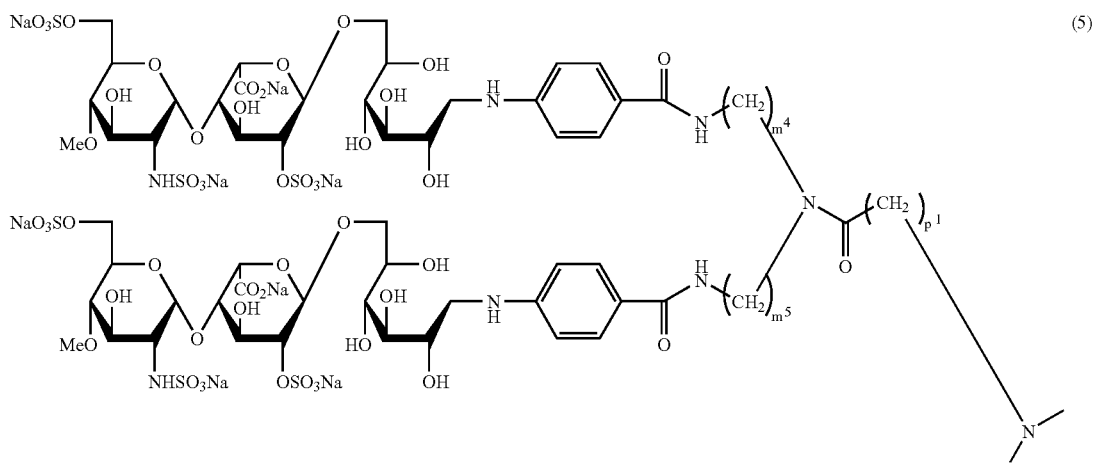

(5)

-continued

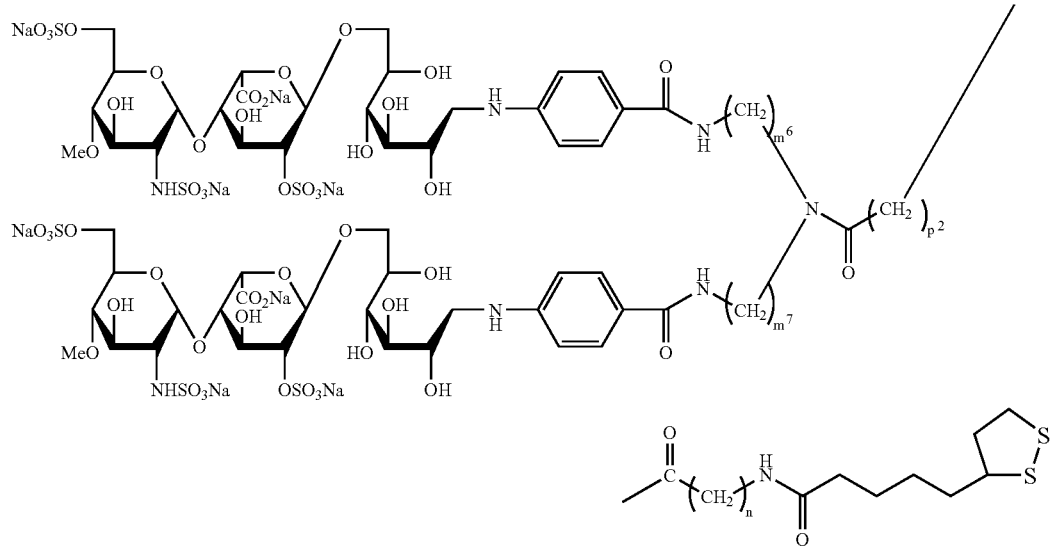

wherein $m^4$, $m^5$, $m^6$, $m^7$, n, $p^1$, and $p^2$ are independently an integer of 1 to 6.

10. The ligand according to claim 9, wherein $m^4$, $m^5$, $m^6$, and $m^7$ are all 2, and n is 1, and $p^1$ and $p^2$ are both 1 in the general formula (5).

11. A method of producing the linker compound of claim 1, comprising:
carrying out a condensation reaction between thioctic acid and an amine compound whose aromatic amino group end is protected by a protecting group which is a t-butoxycarbonyl group, a benzyl group, or an allyl carbamate group, the amine compound being represented by the following general formula (19):

(19)

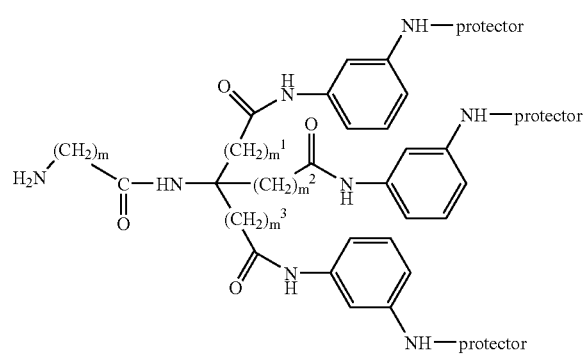

where n, $m^1$, $m^2$ and $m^3$ are independently an integer of 1 to 6; and
deprotecting the protecting group at the aromatic amino group end.

12. A method of producing a ligand, comprising carrying out a reductive amination reaction between the linker compound according to claim 1, and a sugar molecule.

13. A method of immobilizing a ligand containing a sugar molecule on a surface of a support,
which comprises, allowing a solution containing the ligand of claim 5 to come into contact with the surface of the support whose surface has a metal, to form a S-metal bond between a S—S bond contained in the ligand of claim 5 and the metal of the surface of the support, via which S-metal bond, a sugar molecule contained in the ligand of claim 5 is immobilized on the surface of the support.

14. A ligand carrier which comprises the ligand of claim 5 immobilized on a surface of a support whose surface has a metal.

15. The ligand carrier according to claim 14, wherein the support is a sensor chip for a surface plasmon resonance measurement.

16. The ligand carrier according to claim 14, wherein the support is a column for affinity chromatography.

17. A method of immobilizing a ligand containing a sugar molecule on a surface of a support,
which comprises, allowing a solution containing the ligand of claim 7 to come into contact with the surface of the support whose surface has a metal, to form a S-metal bond between a S—S bond contained in the ligand of claim 7 and the metal of the surface of the support, via which S-metal bond, a sugar molecule contained in the ligand of claim 7 is immobilized on the surface of the support.

18. A ligand carrier which comprises the ligand of claim 7 immobilized on a surface of a support whose surface has a metal.

19. The ligand carrier according to claim 18, wherein the support is a sensor chip for a surface plasmon resonance measurement.

20. The ligand carrier according to claim 18, wherein the support is a column for affinity chromatography.

21. A method of immobilizing a ligand containing a sugar molecule on a surface of a support,
which comprises, allowing a solution containing the ligand of claim 9 to come into contact with the surface of the support whose surface has a metal, to form a S-metal bond between a S—S bond contained in the ligand of claim 9 and the metal of the surface of the support, via which S-metal bond, a sugar molecule contained in the ligand of claim 9 is immobillized on the surface of the support.

22. A ligand carrier which comprises the ligand of claim 9 immobilized on a surface of a support whose surface has a metal.

23. The ligand carrier according to claim 22, wherein the support is a sensor chip for a surface plasmon resonance measurement.

24. The ligand carrier according to claim 22, wherein the support is a column for affinity chromatography.

25. A method of producing the linker compound of claim 3, comprising:
carrying out a condensation reaction between thioctic acid and an amine compound whose aromatic amino group end is protected by a protecting group which is a t-butoxycarbonyl group, a benzyl group, or an allyl carbamate group, the amine compound being represented by the following general formula (20):

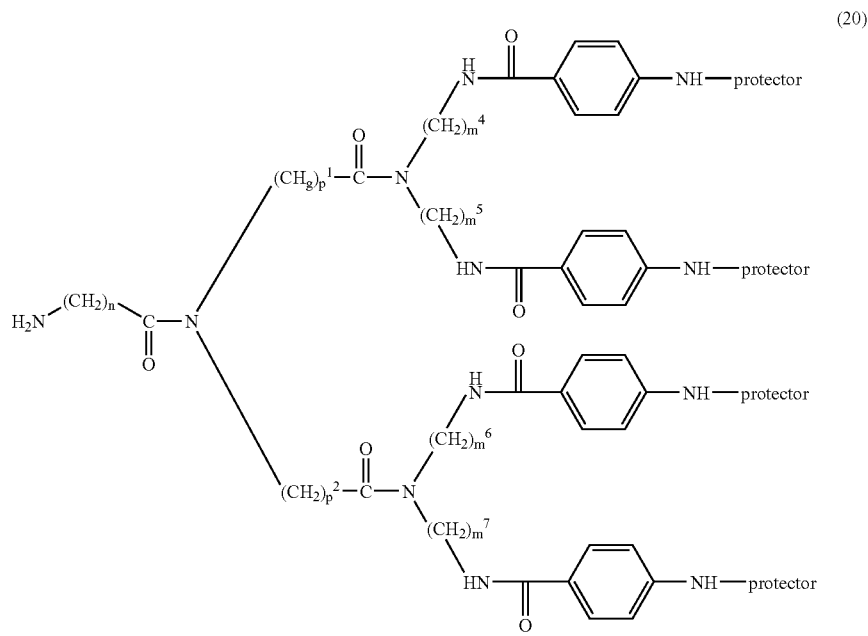

where n, m4, m5, m6, m7, p1, and p2, are independently an integer of 1 to 6; and deprotecting the protecting group at the aromatic amino group end.

* * * * *

UNITED STATES PATENT AND TRADEMARK OFFICE
CERTIFICATE OF CORRECTION

PATENT NO. : 7,320,867 B2  Page 1 of 1
APPLICATION NO. : 10/526775
DATED : January 22, 2008
INVENTOR(S) : Yasuo Suda et al.

It is certified that error appears in the above-identified patent and that said Letters Patent is hereby corrected as shown below:

On Title Page
Please amend the Foreign Application Priority Data on page 1 to read:

Item --(30)    Foreign Application Priority Data

Sep. 9, 2002 (JP) ……………………………… 2002-263412
Jul. 2, 2003 (JP)………………………………. 2003-190568--

Signed and Sealed this

Sixth Day of May, 2008

JON W. DUDAS
*Director of the United States Patent and Trademark Office*